United States Patent
Berger et al.

(10) Patent No.: US 7,368,567 B2
(45) Date of Patent: May 6, 2008

(54) ARYLSULFONYL BENZODIOXANES, BENZOXAZINES AND BENZOTHIAZINES AS 5-HT6 ANTAGONISTS

(75) Inventors: Jacob Berger, Los Altos Hills, CA (US); Shu-Hai Zhao, Sunnyvale, CA (US)

(73) Assignee: Roche Palo Alto LLC, Palo Alto, CA (US)

( * ) Notice: Subject to any disclaimer, the term of this patent is extended or adjusted under 35 U.S.C. 154(b) by 185 days.

(21) Appl. No.: 11/121,873

(22) Filed: May 4, 2005

(65) Prior Publication Data

US 2005/0250943 A1    Nov. 10, 2005

Related U.S. Application Data

(60) Provisional application No. 60/568,314, filed on May 5, 2004.

(51) Int. Cl.

| C07D 265/36 | (2006.01) |
|---|---|
| C07D 498/02 | (2006.01) |
| C07D 321/00 | (2006.01) |
| C07D 323/00 | (2006.01) |
| C07D 327/06 | (2006.01) |
| C07D 327/10 | (2006.01) |
| C07D 339/08 | (2006.01) |
| C07D 341/00 | (2006.01) |
| C07D 343/00 | (2006.01) |
| C07D 409/00 | (2006.01) |
| C07D 411/00 | (2006.01) |
| C07D 495/00 | (2006.01) |

(52) U.S. Cl. .................... 544/105; 549/15; 549/350

(58) Field of Classification Search ............... None
See application file for complete search history.

(56) References Cited

U.S. PATENT DOCUMENTS

| 5,137,901 A | 8/1992 | Junge et al. |
|---|---|---|
| 5,374,643 A | 12/1994 | Atwal et al. |
| 5,412,117 A | 5/1995 | Koga et al. |
| 5,614,633 A | 3/1997 | Koga et al. |
| 5,627,138 A | 5/1997 | Anderson et al. |
| 5,646,308 A | 7/1997 | Koga et al. |
| 5,663,194 A | 9/1997 | Mewshaw |
| 5,719,182 A | 2/1998 | Cousins et al. |
| 5,739,135 A | 4/1998 | Biller et al. |
| 5,869,478 A | 2/1999 | Ding et al. |
| 5,874,446 A | 2/1999 | Koga et al. |
| 5,883,099 A | 3/1999 | Biller et al. |
| 5,935,958 A | 8/1999 | Kozlowski et al. |
| 5,977,167 A | 11/1999 | Koga et al. |
| 6,083,982 A | 7/2000 | Wechter et al. |
| 6,150,402 A | 11/2000 | Wechter et al. |
| 6,214,881 B1 | 4/2001 | Xiang |
| 6,448,243 B1 | 9/2002 | Kitazawa et al. |
| 6,479,536 B1 | 11/2002 | Ohkawa et al. |
| 6,559,144 B2 | 5/2003 | Diefenbach et al. |
| 6,605,632 B1 | 8/2003 | Lesieur et al. |
| 6,613,805 B2 | 9/2003 | Kato et al. |
| 6,638,972 B2 | 10/2003 | Kelly et al. |
| 6,660,752 B2 | 12/2003 | O'Connor et al. |
| 6,706,757 B2 | 3/2004 | Greenblatt et al. |
| 6,784,314 B2 | 8/2004 | Yamashita et al. |
| 2002/0002177 A1 | 1/2002 | Cousins et al. |
| 2004/0024210 A1 | 2/2004 | Johansson et al. |
| 2005/0154053 A1 | 7/2005 | Van Rhijn et al. |

FOREIGN PATENT DOCUMENTS

| EP | 0 488 616 A1 | 6/1992 |
|---|---|---|
| EP | 0 587 180 A2 | 9/1992 |
| EP | 0 747 374 B1 | 12/2001 |
| WO | WO 97/02259 A1 | 1/1997 |
| WO | WO 98/07418 A1 | 2/1998 |
| WO | WO 2005/040355 A2 | 5/2005 |

OTHER PUBLICATIONS

March, Jerry. Advanced Organic Chemistry, Third Edition. John Wiley & Sons, 1985, pp. 476, 484-485.*
Solomons et al. Organic Chemistry, Eight Edition. John Wiley & Sons, 2004, pp. 675-690, 708.*
Fletcher et al. 4-(phenylsulfonyl)piperidines: Novel, Selective, Bioavailable 5-HT2a Receptor Antagonists. Journal of Medicinal chemistry, 2002, 45, 45, 492-503.*
Barta et al. Bioorganic and Medicinal Chemistry Letters, 2001, 11, 2481-83.*
Abdel-Magid, A. F., et al., "Reductive Amination of Aldehydes and Ketones with Sodium Triacetoxyborohydride. Studies on Direct and Indirect Reductive Aminations Procedures[b]", *J. Org. Chem.* (1996) vol. 61, pp. 3849-3862.

(Continued)

*Primary Examiner*—James O. Wilson
*Assistant Examiner*—Noble Jarrell
(74) *Attorney, Agent, or Firm*—Robert C. Hall

(57) ABSTRACT

Compounds of the formula I:

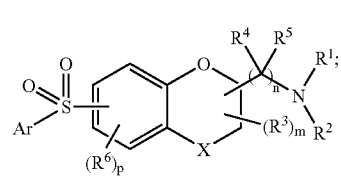

or pharmaceutically acceptable salts, solvates or prodrugs thereof, wherein m, n, p, Ar, X, $R^1$, $R^2$, $R^3$, $R^4$, $R^5$ and $R^6$ are as defined herein. Also provided are compositions comprising, methods of preparing, and methods of using the subject compounds.

23 Claims, No Drawings

OTHER PUBLICATIONS

Choi, J. et al., "Synthetic Studies toward Dideoxynojirimycin Derivatives via Dehydroamino Acid as Key Intermediate", *Bull. Korean Chem. Soc.* (1999) 20(10) pp. 1123-1125.

Feurer, H. et al., "The Reduction of Oximes with Diborane. A New Synthesis of N-Monosubstituted Hydroxylamines", *J. Org. Chem.* (1965) vol. 30(10), pp. 2877-2880.

Kikugawa, Y., et al., "Selective Reduction of Oximes with Pyridine-Borane", *Chem. Letters*, (1977). pp. 1279-1280.

Miguel-Hidalgo, J. J., "SB-271046", *Current Opinion Investig. Drugs*, (2001) vol. 2(1) pp. 118-122.

Roberts, J. D., et. al., "Basic Principles of Organic Chemistry", W. A. Benjamin Inc. (1964), pp. 403, 451 and 665.

Rogers, D. C., et al., "5-HT6 Receptor Antagonists Enhance Retention of a Water Maze Task in the Rat", *Psychopharmacology,* (2001) vol. 158, pp. 114-119.

Smith, M. B. et. al., "March's Advanced Organic Chemistry", J. Wiley & Sons Inc. (2001) pp. 1203 and 1514.

Woolley, M. L., et al., "A Role for 5-HT6 Receptors in Retention of Spatial Learning in the Morris Water Maze", *Neuropharmacology* (2001) vol. 41, pp. 210-219.

Woolley, M. L., et al., "Reversal of a Cholinergic-Induced Deficit in a Rodent Model of Recognition Memory by the Selective 5-HT6 receptor Antagonist Ro 046790", *Psychopharmacology* (2003) vol. 170, pp. 358-367.

\* cited by examiner

ARYLSULFONYL BENZODIOXANES, BENZOXAZINES AND BENZOTHIAZINES AS 5-HT6 ANTAGONISTS

CROSS REFERENCE TO RELATED APPLICATIONS

This application claims benefit under 35 U.S.C. 119(e) of U.S. Provisional Application No. 60/568,314 filed May 05, 2004, which is hereby incorporated by reference in its entirety.

FIELD OF THE INVENTION

This invention relates to substituted benzodioxane and benzoxazine compounds, and associated compositions, methods for use as therapeutic agents, and methods of preparation thereof.

BACKGROUND OF THE INVENTION

The actions of 5-hydroxytryptamine (5-HT) as a major modulatory neurotransmitter in the brain are mediated through a number of receptor families termed 5-HT1, 5-HT2, 5-HT3, 5-HT4, 5-HT5, 5-HT6, and 5-HT7. Based on a high level of 5-HT6 receptor mRNA in the brain, it has been stated that the 5-HT6 receptor may play a role in the pathology and treatment of central nerve system disorders. In particular, 5-HT2-selective and 5-HT6 selective ligands have been identified as potentially useful in the treatment of certain CNS disorders such as Parkinson's disease, Huntington's disease, anxiety, depression, manic depression, psychoses, epilepsy, obsessive compulsive disorders, mood disorders, migraine, Alzheimer's disease (enhancement of cognitive memory), sleep disorders, feeding disorders such as anorexia, bulimia and obesity, panic attacks, akathisia, attention deficit hyperactivity disorder (ADHD), attention deficit disorder (ADD), withdrawal from drug abuse such as cocaine, ethanol, nicotine and benzodiazepines, schizophrenia, and also disorders associated with spinal trauma and/or head injury such as hydrocephalus. Such compounds are also expected to be of use in the treatment of certain gastrointestinal (GI) disorders such as functional bowel disorder. See for example, B. L. Roth et al., J. Pharmacol. Exp. Ther., 1994, 268, pages 1403-14120, D. R. Sibley et al., Mol. Pharmacol., 1993, 43, 320-327, A. J. Sleight et al., Neurotransmission, 1995, 11, 1-5, and A. J. Sleight et al., Serotonin ID Research Alert, 1997, 2(3), 115-8.

While some 5-HT6 and 5-HT2A modulators have been disclosed, there continues to be a need for compounds that are useful for modulating the 5-HT6 receptor, the 5-HT2A receptor, or both.

SUMMARY

The invention provides compounds of the formula I:

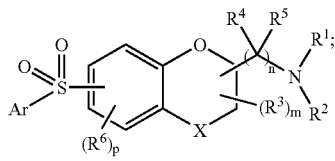

or a pharmaceutically acceptable salt thereof, wherein:
m is from 0 to 3;
n is from 1 to 3;
p is from 0 to 3;

Ar is optionally substituted aryl or optionally substituted heteroaryl;

X is —O—, —S— or —NR$^a$— wherein R$^a$ is hydrogen, $C_{1-6}$alkyl, $C_{1-6}$alkylcarbonyl or $C_{1-6}$alkylsulfonyl;

R$^1$ and R$^2$ each independently is hydrogen, $C_{1-6}$alkyl, $C_{1-6}$alkoxy-$C_{1-6}$alkyl, or hydroxy-$C_{1-6}$alkyl;

or one of R$^1$ and R$^2$ is hydrogen or $C_{1-6}$alkyl and the other is $C_{1-6}$alkylcarbonyl, $C_{3-8}$cycloalkyl, aryl-$C_{1-6}$alkyl, or a five- or six-membered heteroaryl or heterocyclyl that contains one or two nitrogens;

or R$^1$ and R$^2$ together with the nitrogen to which they are attached may form a three- to seven-membered ring that optionally contains an additional heteroatom selected from N, O and S;

or R$^1$ and R$^2$ together with the nitrogen to which they are attached may form a guanidinyl group, an amidinyl group, a carbamyl group, or a urea group;

each R$^3$ is independently $C_{1-6}$alkyl, hydroxy-$C_{1-6}$alkyl or $C_{1-6}$alkoxy-$C_{1-6}$alkyl;

or two of R$^3$ together with the atoms to which they are attached may form a $C_{4-6}$carbocyclic ring;

or one of R$^3$ together with one of R$^1$ and R$^2$ and the atoms to which they are attached may form a five or six-membered ring;

R$^4$ and R$^5$ each independently is hydrogen or $C_{1-6}$alkyl;

or one of R$^4$ and R$^5$ together with one of R$^1$ and R$^2$ and the atoms to which they are attached may form a five or six-membered ring;

or R$^4$ and R$^5$ together may form an imino group of the formula =NR$^f$ wherein R$^f$ is hydrogen or $C_{1-6}$alkyl; and each R$^6$ is independently halo, $C_{1-6}$alkyl, halo-$C_{1-6}$alkyl, hetero-$C_{1-6}$alkyl, cyano, —SO$_2$R$^b$, —C(=O)—NR$^c$R$^d$, —SR$^c$, —C(=O)—R$^c$, where each of R$^b$, R$^c$ and R$^d$ is independently hydrogen or $C_{1-6}$alkyl.

The invention also provides methods for preparing the aforementioned compounds. The subject methods may comprise, in certain embodiments, reacting a compound of the formula 1c:

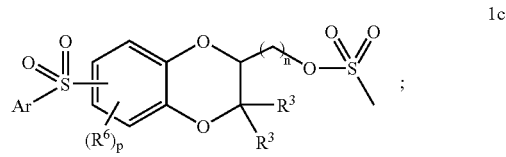

wherein n, p, Ar, R$^3$ and R$^6$ are as defined herein, with an amine of formula g:

R$^1$R$^2$NH g;

wherein R$^1$ and R$^2$ are as defined herein, to form a compound of formula 1d:

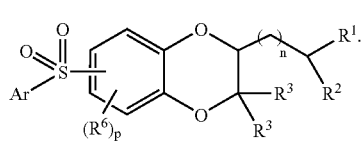

The invention further provides compositions comprising, and methods for using the aforementioned compounds.

DETAILED DESCRIPTION OF THE INVENTION

The invention provides substituted quinolinone compounds, associated compositions, methods for use as therapeutic agents, and methods of preparation thereof. In specific embodiments the invention provides piperazinyl-substituted quinolinone compounds and associated pharmaceutical compositions, and methods for using the same in the treatment of central nervous system (CNS) diseases and gastrointestinal tract disorders.

All patents and publications cited in this disclosure are incorporated herein by reference in their entirety.

Definitions

Unless otherwise stated, the following terms used in this Application, including the specification and claims, have the definitions given below. It must be noted that, as used in the specification and the appended claims, the singular forms "a", "an," and "the" include plural referents unless the context clearly dictates otherwise.

"Agonist" refers to a compound that enhances the activity of another compound or receptor site.

"Alkyl" means the monovalent linear or branched saturated hydrocarbon moiety, consisting solely of carbon and hydrogen atoms, having from one to twelve carbon atoms. "Lower alkyl" refers to an alkyl group or moiety of one to six carbon atoms, i.e. $C_1$-$C_6$alkyl. Examples of alkyl groups include, but are not limited to, methyl, ethyl, propyl, isopropyl, isobutyl, sec-butyl, tert-butyl, pentyl, n-hexyl, octyl, dodecyl, and the like.

"Alkylene" means a linear saturated divalent hydrocarbon radical of one to six carbon atoms or a branched saturated divalent hydrocarbon radical of three to six carbon atoms, e.g., methylene, ethylene, 2,2-dimethylethylene, propylene, 2-methylpropylene, butylene, pentylene, and the like.

"Alkenylene" means a linear unsaturated divalent hydrocarbon radical of two to six carbon atoms or a branched saturated divalent hydrocarbon radical of three to six carbon atoms, e.g., ethenylene (—CH=CH—), 2,2-dimethylethenylene, propenylene, 2-methylpropenylene, butenylene, pentenylene, and the like.

"Alkoxy" means a moiety of the formula —OR, wherein R is an alkyl moiety as defined herein. Examples of alkoxy moieties include, but are not limited to, methoxy, ethoxy, isopropoxy, and the like.

"Alkoxyalkyl" means a moiety of the formula —R'—R", where R' is alkylene and R" is alkoxy as defined herein. Exemplary alkoxyalkyl groups include, by way of example, 2-methoxyethyl, 3-methoxypropyl, 1-methyl-2-methoxyethyl, 1-(2-methoxyethyl)-3-methoxypropyl, and 1-(2-methoxyethyl)-3-methoxypropyl.

"Alkylcarbonyl" means a moiety of the formula —R'—R", where R' is oxo and R" is alkyl as defined herein.

"Alkylsulfonyl" means a moiety of the formula —R'—R", where $R^1$ is —$SO_2$— and R" is alkyl as defined herein.

"Alkylsulfonylalkyl" means a moiety of the formula $R^a$—$SO_2$—$R^b$—, where $R^a$ is alkyl and $R^b$ is alkylene as defined herein. Exemplary alkylsulfonylalkyl groups include, by way of example, 3-methanesulfonylpropyl, 2-methanesulfonylethyl, 2-methanesulfonylpropy, and the like.

"Aminoalkyl" means a group —R—R' wherein R' is amino and R is alkylene as defined herein. "Aminoalkyl" includes aminomethyl, aminoethyl, 1-aminopropyl, 2-aminopropyl, and the like. The amino moiety of "aminoalkyl" may be substituted once or twice with alkyl to provide "alkylaminoalkyl" and "dialkylaminoalkyl" respectively.

"Alkylaminoalkyl" includes methylaminomethyl, methylaminoethyl, methylaminopropyl, ethylaminoethyl and the like. "Dialkylaminoalkyl" includes dimethylaminomethyl, dimethylaminoethyl, dimethylaminopropyl, N-methyl-N-ethylaminoethyl, and the like.

"Amidinyl" means a group of the formula:

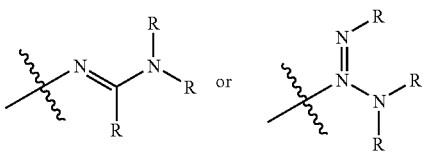

wherein each R independently is hydrogen or alkyl as defined herein.

"Amidinylalkyl" means a group —R—R' wherein R' is amidinyl as defined herein and R is alkylene.

"Amido" means a group —C(O)—NRR' wherein R and R' each independently is hydrogen or alkyl.

"Antagonist" refers to a compound that diminishes or prevents the action of another compound or receptor site.

"Aryl" means a monovalent cyclic aromatic hydrocarbon moiety consisting of a mono-, bi- or tricyclic aromatic ring. The aryl group can be optionally substituted as defined herein. Examples of aryl moieties include, but are not limited to, optionally substituted phenyl, naphthyl, phenanthryl, fluorenyl, indenyl, pentalenyl, azulenyl, oxydiphenyl, biphenyl, methylenediphenyl, aminodiphenyl, diphenylsulfidyl, diphenylsulfonyl, diphenylisopropylidenyl, benzodioxanyl, benzofuranyl, benzodioxylyl, benzopyranyl, benzoxazinyl, benzoxazinonyl, benzopiperadinyl, benzopiperazinyl, benzopyrrolidinyl, benzomorpholinyl, methylenedioxyphenyl, ethylenedioxyphenyl, and the like, including partially hydrogenated derivatives thereof.

"Aryloxy" means a moiety of the formula —OR, wherein R is an aryl moiety as defined herein.

"Arylalkyl" and "Aralkyl", which may be used interchangeably, mean a radical-$R^aR^b$ where $R^a$ is an alkylene group and $R^b$ is an aryl group as defined herein; e.g., phenylalkyls such as benzyl, phenylethyl, 3-(3-chlorophenyl)-2-methylpentyl, and the like are examples of arylalkyl.

"Aralkoxy" means a moiety of the formula —OR, wherein R is an aralkyl moiety as defined herein.

"Carbamyl means a group of the formula:

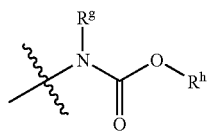

wherein $R^g$ and $R^h$ each independently is hydrogen or alkyl.

"Cyanoalkyl" means a moiety of the formula —R'—R", where R' is alkylene as defined herein and R" is cyano or nitrile.

"Cycloalkyl" means a monovalent saturated carbocyclic moiety consisting of mono- or bicyclic rings. Cycloalkyl can optionally be substituted with one or more substituents, wherein each substituent is independently hydroxy, alkyl, alkoxy, halo, haloalkyl, amino, monoalkylamino, or dialkylamino, unless otherwise specifically indicated. Examples of cycloalkyl moieties include, but are not limited to, cyclopropyl, cyclobutyl, cyclopentyl, cyclohexyl, cycloheptyl, and the like, including partially unsaturated derivatives thereof.

"Cycloalkylalkyl" means a moiety of the formula —R'—R", where R' is alkylene and R" is cycloalkyl as defined herein.

"Guanidinyl" as used herein means a group of the formula:

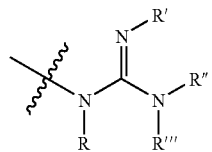

wherein R, R', R" and R'" each independently is hydrogen or alkyl.

"Heteroalkyl" means an alkyl radical as defined herein wherein one, two or three hydrogen atoms have been replaced with a substituent independently selected from the group consisting of —OR$^a$, —NR$^b$R$^c$, and —S(O)$_n$R$^d$ (where n is an integer from 0 to 2), with the understanding that the point of attachment of the heteroalkyl radical is through a carbon atom, wherein R$^a$ is hydrogen, acyl, alkyl, cycloalkyl, or cycloalkylalkyl; R$^b$ and R$^c$ are independently of each other hydrogen, acyl, alkyl, cycloalkyl, or cycloalkylalkyl; and when n is 0, R$^d$ is hydrogen, alkyl, cycloalkyl, or cycloalkylalkyl, and when n is 1 or 2, R$^d$ is alkyl, cycloalkyl, cycloalkylalkyl, amino, acylamino, monoalkylamino, or dialkylamino. Representative examples include, but are not limited to, 2-hydroxyethyl, 3-hydroxypropyl, 2-hydroxy-1-hydroxymethylethyl, 2,3-dihydroxypropyl, 1-hydroxymethylethyl, 3-hydroxybutyl, 2,3-dihydroxybutyl, 2-hydroxy-1-methylpropyl, 2-aminoethyl, 3-aminopropyl, 2-methylsulfonylethyl, aminosulfonylmethyl, aminosulfonylethyl, aminosulfonylpropyl, methylaminosulfonylmethyl, methylaminosulfonylethyl, methylaminosulfonylpropyl, and the like.

"Heteroaryl" means a monocyclic or bicyclic radical of 5 to 12 ring atoms having at least one aromatic ring containing one, two, or three ring heteroatoms selected from N, O, or S, the remaining ring atoms being C, with the understanding that the attachment point of the heteroaryl radical will be on an aromatic ring. The heteroaryl ring may be optionally substituted as defined herein. Examples of heteroaryl moieties include, but are not limited to, optionally substituted imidazolyl, oxazolyl, isoxazolyl, thiazolyl, isothiazolyl, oxadiazolyl, thiadiazolyl, pyrazinyl, thienyl, benzothienyl, thiophenyl, furanyl, pyranyl, pyridyl, pyrrolyl, pyrazolyl, pyrimidyl, quinolinyl, isoquinolinyl, benzofuryl, benzothiophenyl, benzothiopyranyl, benzimidazolyl, benzooxazolyl, benzooxadiazolyl, benzothiazolyl, benzothiadiazolyl, benzopyranyl, indolyl, isoindolyl, triazolyl, triazinyl, quinoxalinyl, purinyl, quinazolinyl, quinolizinyl, naphthyridinyl, pteridinyl, carbazolyl, azepinyl, diazepinyl, acridinyl and the like, including partially hydrogenated derivatives thereof.

"Heteroaryloxy" means a moiety of the formula —OR, wherein R is a heteroaryl moiety as defined herein.

"Heteroarylalkyl" and "Heteroaralkyl", which may be used interchangeably, mean a radical-R$^a$R$^b$ where R$^a$ is an alkylene group and R$^b$ is a heteroaryl group as defined herein.

"Heteroaralkoxy" means a moiety of the formula —OR, wherein R is a heteroaralkyl moiety as defined herein.

The terms "halo" and "halogen", which may be used interchangeably, refer to a substituent fluoro, chloro, bromo, or iodo.

"Haloalkyl" means alkyl as defined herein in which one or more hydrogen has been replaced with same or different halogen. Exemplary haloalkyls include —CH$_2$Cl, —CH$_2$CF$_3$, —CH$_2$CCl$_3$, perfluoroalkyl (e.g., —CF$_3$), and the like.

"Haloalkoxy" means a moiety of the formula —OR, wherein R is a haloalkyl moiety as defined herein. Examples of alkoxy moieties include, but are not limited to, methoxy, ethoxy, isopropoxy, and the like.

"Hydroxyalkyl" refers to a subset of heteroalkyl and refers in particular to an alkyl moiety as defined herein that is substituted with one or more, preferably one, two or three hydroxy groups, provided that the same carbon atom does not carry more than one hydroxy group. Representative examples include, but are not limited to, hydroxymethyl, 2-hydroxyethyl, 2-hydroxypropyl, 3-hydroxypropyl, 1-(hydroxymethyl)-2-methylpropyl, 2-hydroxybutyl, 3-hydroxybutyl, 4-hydroxybutyl, 2,3-dihydroxypropyl, 2-hydroxy-1-hydroxymethylethyl, 2,3-dihydroxybutyl, 3,4-dihydroxybutyl and 2-(hydroxymethyl)-3-hydroxypropyl "Heterocycloamino" means a saturated ring wherein at least one ring atom is N, NH or N-alkyl and the remaining ring atoms form an alkylene group.

"Heterocyclyl" means a monovalent saturated moiety, consisting of one to three rings, incorporating one, two, or three or four heteroatoms (chosen from nitrogen, oxygen or sulfur). The heterocyclyl ring may be optionally substituted as defined herein. Examples of heterocyclyl moieties include, but are not limited to, optionally substituted piperidinyl, piperazinyl, homopiperazinyl, azepinyl, pyrrolidinyl, pyrazolidinyl, imidazolinyl, imidazolidinyl, pyridinyl, pyridazinyl, pyrimidinyl, oxazolidinyl, isoxazolidinyl, morpholinyl, thiazolidinyl, isothiazolidinyl, quinuclidinyl, quinolinyl, isoquinolinyl, benzimidazolyl, thiadiazolylidinyl, benzothiazolidinyl, benzoazolylidinyl, dihydrofuryl, tetrahydrofuryl, dihydropyranyl, tetrahydropyranyl, thiamorpholinyl, thiamorpholinylsulfoxide, thiamorpholinylsulfone, dihydroquinolinyl, dihydrisoquinolinyl, tetrahydroquinolinyl, tetrahydrisoquinolinyl, and the like.

"Heterocyclylalkyl" means a group —R—R' wherein R' is heterocyclyl as defined herein and R is alkylene.

"Imidazolinyl" as used herein means a group of the formula:

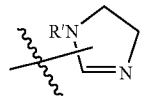

wherein R' is hydrogen or alkyl. Imidazolinyl groups may be optionally substituted as defined herein.

"Imidazolinylalkyl" means a group —R—R' wherein R' is imidazolinyl as defined herein and R is alkylene.

"Imidazolinylaminoalkyl" means a group —R—R'—R" wherein R" is imidazolinyl as defined herein, R' is amino, and R is alkylene. The amino moiety of "imidazolinylaminoalkyl" may be optionally substituted with alkyl.

"Pyrimidinylaminoalkyl" means a group —R—R'—R" wherein R" is pyrinmidinyl (preferably pyrimidin-2-yl), R' is amino, and R is alkylene. The pyrimidinyl moiety of "pyrimidinylaminoalkyl" may be optionally substituted as defined herein, and the amino moiety of "pyrimidinylaminoalkyl" may be optionally substituted with alkyl.

"Tetrahydropyrimidinyl" means 1,4,5,6-tetrahydropyrimidinyl, preferably 1,4,5,6-tetrahydropyrimidin-2-yl, and may be optionally substituted as defined herein. "Tetrahydropyrimidinyl" includes 5,5-dimethyl-1,4,5,6-tetrahydropyrimidin-2-yl.

"Tetrahydropyrimidinylaminoalkyl" means a group —R—R'—R" wherein R" is tetrahydropyrimidinyl, R' is amino, and R is alkylene. The amino moiety of "tetrahydropyrimidinylaminoalkyl" may be optionally substituted with alkyl.

"Urea" means a group of the formula:

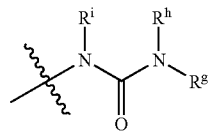

wherein $R^g$, $R^h$ and $R^i$ each independently is hydrogen or alkyl.

"Urealkyl" means a group R—R' wherein R' is urea and R is alkylene.

"Optionally substituted", when used in association with "aryl", "phenyl", "heteroaryl" or "heterocyclyl", means an aryl, phenyl, heteroaryl or heterocyclyl which is optionally substituted independently with one to four substituents, preferably one or two substituents selected from alkyl, cycloalkyl, cycloalkylalkyl, heteroalkyl, hydroxyalkyl, halo, nitro, cyano, hydroxy, alkoxy, amino, acylamino, monoalkylamino, di-alkylamino, haloalkyl, haloalkoxy, heteroalkyl, —COR (where R is hydrogen, alkyl, phenyl or phenylalkyl), —(CR'R")$_n$—COOR (where n is an integer from 0 to 5, R' and R" are independently hydrogen or alkyl, and R is hydrogen, alkyl, cycloalkyl, cycloalkylalkyl, phenyl or phenylalkyl), or —CR'R")$_n$—CONR$^a$R$^b$ (where n is an integer from 0 to 5, R' and R" are independently hydrogen or alkyl, and R$^a$ and R$^b$ are, independently of each other, hydrogen, alkyl, cycloalkyl, cycloalkylalkyl, phenyl or phenylalkyl).

"Leaving group" means the group with the meaning conventionally associated with it in synthetic organic chemistry, i.e., an atom or group displaceable under substitution reaction conditions. Examples of leaving groups include, but are not limited to, halogen, alkane- or arylenesulfonyloxy, such as methanesulfonyloxy, ethanesulfonyloxy, thiomethyl, benzenesulfonyloxy, tosyloxy, and thienyloxy, dihalophosphinoyloxy, optionally substituted benzyloxy, isopropyloxy, acyloxy, and the like.

"Modulator" means a molecule that interacts with a target. The interactions include, but are not limited to, agonist, antagonist, and the like, as defined herein.

"Optional" or "optionally" means that the subsequently described event or circumstance may but need not occur, and that the description includes instances where the event or circumstance occurs and instances in which it does not.

"Disease" and "Disease state" means any disease, condition, symptom, disorder or indication.

"Inert organic solvent" or "inert solvent" means the solvent is inert under the conditions of the reaction being described in conjunction therewith, including for example, benzene, toluene, acetonitrile, tetrahydrofuran, N,N-dimethylformamide, chloroform, methylene chloride or dichloromethane, dichloroethane, diethyl ether, ethyl acetate, acetone, methyl ethyl ketone, methanol, ethanol, propanol, isopropanol, tert-butanol, dioxane, pyridine, and the like. Unless specified to the contrary, the solvents used in the reactions of the present invention are inert solvents.

"Pharmaceutically acceptable" means that which is useful in preparing a pharmaceutical composition that is generally safe, non-toxic, and neither biologically nor otherwise undesirable and includes that which is acceptable for veterinary as well as human pharmaceutical use.

"Pharmaceutically acceptable salts" of a compound means salts that are pharmaceutically acceptable, as defined herein, and that possess the desired pharmacological activity of the parent compound. Such salts include: acid addition salts formed with inorganic acids such as hydrochloric acid, hydrobromic acid, sulfuric acid, nitric acid, phosphoric acid, and the like; or formed with organic acids such as acetic acid, benzenesulfonic acid, benzoic, camphorsulfonic acid, citric acid, ethanesulfonic acid, fumaric acid, glucoheptonic acid, gluconic acid, glutamic acid, glycolic acid, hydroxynaphtoic acid, 2-hydroxyethanesulfonic acid, lactic acid, maleic acid, malic acid, malonic acid, mandelic acid, methanesulfonic acid, muconic acid, 2-naphthalenesulfonic acid, propionic acid, salicylic acid, succinic acid, tartaric acid, p-toluenesulfonic acid, trimethylacetic acid, and the like; or salts formed when an acidic proton present in the parent compound either is replaced by a metal ion, e.g., an alkali metal ion, an alkaline earth ion, or an aluminum ion; or coordinates with an organic or inorganic base. Acceptable organic bases include diethanolamine, ethanolamine, N-methylglucamine, triethanolamine, tromethamine, and the like. Acceptable inorganic bases include aluminum hydroxide, calcium hydroxide, potassium hydroxide, sodium carbonate and sodium hydroxide.

The preferred pharmaceutically acceptable salts are the salts formed from acetic acid, hydrochloric acid, sulphuric acid, methanesulfonic acid, maleic acid, phosphoric acid, tartaric acid, citric acid, sodium, potassium, calcium, zinc, and magnesium.

It should be understood that all references to pharmaceutically acceptable salts include solvent addition forms (solvates) or crystal forms (polymorphs) as defined herein, of the same acid addition salt.

The terms "pro-drug" and "prodrug", which may be used interchangeably herein, refer to any compound which releases an active parent drug according to formula I in vivo when such prodrug is administered to a mammalian subject. Prodrugs of a compound of formula I are prepared by modifying one or more functional group(s) present in the compound of formula I in such a way that the modification(s) may be cleaved in vivo to release the parent compound. Prodrugs include compounds of formula I wherein a hydroxy, amino, or sulfhydryl group in a compound of Formula I is bonded to any group that may be cleaved in vivo to regenerate the free hydroxyl, amino, or sulfhydryl group, respectively. Examples of prodrugs include, but are not limited to, esters (e.g., acetate, formate, and benzoate derivatives), carbamates (e.g., N,N-dimethylaminocarbonyl) of hydroxy functional groups in compounds of formula I, N-acyl derivatives (e.g. N-acetyl) N-Mannich bases, Schiff bases and enaminones of amino functional groups, oximes, acetals, ketals and enol esters of ketone and aldehyde functional groups in compounds of Formula I, and the like, see Bundegaard, H. "Design of Prodrugs" p1-92, Elsevier, New York-Oxford (1985), and the like.

"Protective group" or "protecting group" means the group which selectively blocks one reactive site in a multifunctional compound such that a chemical reaction can be carried out selectively at another unprotected reactive site in the meaning conventionally associated with it in synthetic chemistry. Certain processes of this invention rely upon the protective groups to block reactive nitrogen and/or oxygen atoms present in the reactants. For example, the terms "amino-protecting group" and "nitrogen protecting group" are used interchangeably herein and refer to those organic groups intended to protect the nitrogen atom against undesirable reactions during synthetic procedures. Exemplary nitrogen protecting groups include, but are not limited to, trifluoroacetyl, acetamido, benzyl (Bn), benzyloxycarbonyl (carbobenzyloxy, CBZ), p-methoxybenzyloxycarbonyl, p-nitrobenzyloxycarbonyl, tert-butoxycarbonyl (BOC), and the like. Persons skilled in the art will know how to choose a group for the ease of removal and for the ability to withstand the following reactions.

"Solvates" means solvent additions forms that contain either stoichiometric or non stoichiometric amounts of solvent. Some compounds have a tendency to trap a fixed molar ratio of solvent molecules in the crystalline solid state, thus forming a solvate. If the solvent is water the solvate formed is a hydrate, when the solvent is alcohol, the solvate formed is an alcoholate. Hydrates are formed by the combination of one or more molecules of water with one of the substances in which the water retains its molecular state as $H_2O$, such combination being able to form one or more hydrate.

"Subject" means mammals and non-mammals. Mammals means any member of the mammalia class including, but not limited to, humans; non-human primates such as chimpanzees and other apes and monkey species; farm animals such as cattle, horses, sheep, goats, and swine; domestic animals such as rabbits, dogs, and cats; laboratory animals including rodents, such as rats, mice, and guinea pigs; and the like. Examples of non-mammals include, but are not limited to, birds, and the like. The term "subject" does not denote a particular age or sex.

"Treating" or "treatment" of a disease state includes:
(i) preventing the disease state, i.e. causing the clinical symptoms of the disease state not to develop in a subject that may be exposed to or predisposed to the disease state, but does not yet experience or display symptoms of the disease state.
(ii) inhibiting the disease state, i.e., arresting the development of the disease state or its clinical symptoms, or
(iii) relieving the disease state, i.e., causing temporary or permanent regression of the disease state or its clinical symptoms.

The terms "treating", "contacting" and "reacting" when referring to a chemical reaction means adding or mixing two or more reagents under appropriate conditions to produce the indicated and/or the desired product. It should be appreciated that the reaction which produces the indicated and/or the desired product may not necessarily result directly from the combination of two reagents which were initially added, i.e., there may be one or more intermediates which are produced in the mixture which ultimately leads to the formation of the indicated and/or the desired product.

Nomenclature and Structures

In general, the nomenclature used in this Application is based on AUTONOM™ v.4.0, a Beilstein Institute computerized system for the generation of IUPAC systematic nomenclature. Chemical structures shown herein were prepared using ISIS® version 2.2. Any open valency appearing on a carbon, oxygen or nitrogen atom in the structures herein indicates the presence of a hydrogen atom. Numbering of ring positions of the benzodioxane, benzoxazine and benzothiazine compounds of the invention is done according to the formula:

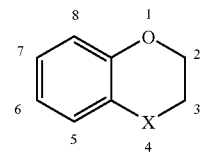

Compounds

The invention provides compounds of the formula I:

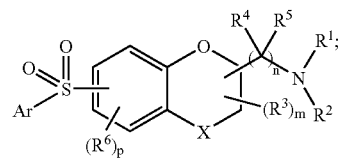

or a pharmaceutically acceptable salt thereof, wherein:
m is from 0 to 3;
n is from 1 to 3;
p is from 0 to 3;
Ar is optionally substituted aryl or optionally substituted heteroaryl;
X is —O—, —S— or —NR— wherein $R^a$ is hydrogen, $C_{1-6}$alkyl, $C_{1-6}$alkylcarbonyl or $C_{1-6}$alkylsulfonyl;
$R^1$ and $R^2$ each independently is hydrogen, $C_{1-6}$alkyl, $C_{1-6}$alkoxy-$C_{1-6}$alkyl, or hydroxy-$C_{1-6}$alkyl;
or one of $R^1$ and $R^2$ is hydrogen or $C_{1-6}$alkyl and the other is $C_{1-6}$alkylcarbonyl, $C_{3-8}$cycloalkyl, aryl-$C_{1-6}$alkyl, hydroxy, or a five- or six-membered heteroaryl or heterocyclyl that contains one or two nitrogens;
or $R^1$ and $R^2$ together with the nitrogen to which they are attached may form a three- to seven-membered ring that optionally contains an additional heteroatom selected from N, O and S;
or $R^1$ and $R^2$ together with the nitrogen to which they are attached may form a guanidinyl group, an amidinyl group, a carbamyl group, or a urea group;
each $R^3$ is independently $C_{1-6}$alkyl, hydroxy-$C_{1-6}$alkyl or $C_{1-6}$alkoxy-$C_{1-6}$alkyl;
or two of $R^3$ together with the atoms to which they are attached may form a $C_{4-6}$carbocyclic ring;
or one of $R^3$ together with one of $R^1$ and $R^2$ and the atoms to which they are attached may form a five or six-membered ring;
$R^4$ and $R^5$ each independently is hydrogen or $C_{1-6}$alkyl;
or one of $R^4$ and $R^5$ together with one of $R^1$ and $R^2$ and the atoms to which they are attached may form a five or six-membered ring;
or $R^4$ and $R^5$ together may form =$NR^f$ wherein $R^f$ is hydrogen or $C_{1-6}$alkyl; and
each $R^6$ is independently halo, $C_{1-6}$alkyl, halo-$C_{1-6}$alkyl, hetero-$C_{1-6}$alkyl, cyano, —$SO_2R^b$, —C(=O)—$NR^cR^d$, —$SR^c$, —C(=O)—$R^c$, where each of $R^b$, $R^c$ and $R^d$ is independently hydrogen or $C_{1-6}$alkyl.

It is to be understood that the scope of this invention encompasses not only the various isomers which may exist but also the various mixture of isomers which may be formed. Furthermore, the scope of the invention also encompasses solvates, salts and prodrugs of the subject compounds.

In many embodiments of formula I, X is —O—.

In certain embodiments of the invention, the subject compounds are of the formula II:

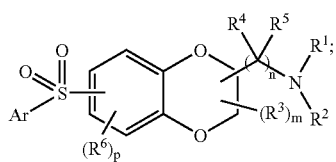

wherein m, n, p, $R^1$, $R^2$, $R^3$, $R^4$, $R^5$ and $R^6$ are as defined herein.

In certain embodiments of formula I or formula II, $R^4$ and $R^5$ are hydrogen.

In certain embodiments of formula I or formula II, m is 0.

In certain embodiments of formula I or formula II, n is 1 or 2. Preferably n is 1.

In certain embodiments of formula I or formula II, p is 0.

In certain embodiments of formula I or formula II, $R^1$ and $R^2$ each independently is hydrogen or $C_{1-6}$alkyl, or $R^1$ and $R^2$ together with the nitrogen to which they are attached form a three, four, five or six-membered ring.

In certain embodiments of formula I or formula II, $R^1$ and $R^2$ each independently is hydrogen or $C_{1-6}$alkyl.

In certain embodiments of formula I or formula II, $R^1$ and $R^2$ together with the nitrogen to which they are attached form a three, four, five or six-membered ring.

In certain embodiments of formula I or formula II, Ar is optionally substituted phenyl.

In certain embodiments of formula I or formula II, $R^4$ and $R^5$ together form =NR' wherein R' is hydrogen or $C_{1-6}$alkyl.

In certain embodiments of formula I or formula II, one of $R^1$ and $R^2$ is hydrogen or $C_{1-6}$alkyl and the other is $C_{1-6}$alkylcarbonyl, $C_{3-8}$cycloalkyl, aryl-$C_{1-6}$alkyl, hydroxy, or a five- or six-membered heteroaryl or heterocyclyl that contains one or two nitrogens.

In certain embodiments of formula I or formula II, one of $R^4$ and $R^5$ together with one of $R^1$ and $R^2$ and the atoms to which they are attached form a five or six-membered ring.

In certain embodiments of formula I or formula II, $R^1$ and $R^2$ together with the nitrogen to which they are attached form a guanidinyl group, an amidinyl group, a carbamyl group, or a urea group. Preferably in such embodiments, $R^1$ and $R^2$ together with the nitrogen to which they are attached form a guanidinyl group.

In certain embodiments of formula I or formula II, $R^1$ and $R^2$ together with the nitrogen to which they are attached form a three- to seven-membered ring that optionally contains an additional heteroatom selected from N, O and S.

In certain embodiments of formula I or formula II, $R^1$ and $R^2$ together with the nitrogen to which they are attached form a three-membered ring.

In certain embodiments of formula I or formula II, $R^1$ and $R^2$ together with the nitrogen to which they are attached form a four-membered ring.

In certain embodiments of formula I or formula II, $R^1$ and $R^2$ together with the nitrogen to which they are attached form a five-membered ring.

In certain embodiments of formula I or formula II, $R^1$ and $R^2$ together with the nitrogen to which they are attached form a six-membered ring.

In certain embodiments of formula I or formula II, m is 1 and $R^3$ is alkyl.

In certain embodiments of formula I or formula II, m is 1 and one of $R^1$ and $R^2$ together with $R^3$ and the atoms to which they are attached form a five or six membered ring.

In certain embodiments of formula I or formula II, n is 1, m is 0, p is 0, and $R^4$ and $R^5$ are hydrogen.

In certain embodiments of formula I or formula II, n is 1, m is 0, p is 0, $R^4$ and $R^5$ are hydrogen, and Ar is optionally substituted phenyl.

In certain embodiments of formula I or formula II, n is 1, m is 0, p is 0, $R^4$ and $R^5$ are hydrogen, Ar is optionally substituted phenyl, and $R^1$ and $R^2$ each independently is hydrogen or $C_{1-6}$alkyl.

In certain embodiments of formula I or formula II, n is 1, m is 0, p is 0, $R^4$ and $R^5$ are hydrogen, Ar is optionally substituted phenyl, and $R^1$ and $R^2$ together with the nitrogen to which they are attached form a three- to seven-membered ring that optionally contains an additional heteroatom selected from N, O and S.

In certain embodiments of formula I or formula II, n is 1, m is 0, p is 0, $R^4$ and $R^5$ are hydrogen, Ar is optionally substituted phenyl, and $R^1$ and $R^2$ together with the nitrogen to which they are attached form a guanidinyl group, an amidinyl group, or a urea group. In such embodiments, $R^1$ and $R^2$ together with the nitrogen to which they are attached preferably form a guanidinyl group.

In certain embodiments of formula I or formula II, n is 1, m is 0, p is 0, $R^4$ and $R^5$ are hydrogen, Ar is optionally substituted phenyl, one of $R^1$ and $R^2$ is hydrogen or $C_{1-6}$alkyl and the other is $C_{1-6}$alkylcarbonyl, $C_{3-8}$cycloalkyl, aryl-$C_{1-6}$alkyl, or a five- or six-membered heteroaryl or heterocyclyl that contains one or two nitrogens. Preferred heteroaryl include imidazolyl, pyrazolyl, pyridyl and pyrimidyl. Preferred heterocyclyl include imidazolinyl and tetrahydropyrimidinyl.

In certain embodiments of formula I or formula II, n is 1, m is 0, p is 0, $R^4$ and $R^5$ are hydrogen, Ar is optionally substituted phenyl, one of $R^1$ and $R^2$ is hydrogen or $C_{1-6}$alkyl and the other is $C_{1-6}$alkylcarbonyl. Preferably in such embodiments, $R^1$ is hydrogen and $R^2$ is acetyl.

In certain embodiments of formula I or formula II, n is 1, m is 0, p is 0, $R^4$ and $R^5$ are hydrogen, Ar is optionally substituted phenyl, one of $R^1$ and $R^2$ is hydrogen or $C_{1-6}$alkyl and the other is $C_{3-8}$cycloalkyl.

In certain embodiments of formula I or formula II, n is 1, m is 0, p is 0, $R^4$ and $R^5$ are hydrogen, Ar is optionally substituted phenyl, one of $R^1$ and $R^2$ is hydrogen or $C_{1-6}$alkyl and the other is aryl-$C_{1-6}$alkyl. Preferably in such embodiments, $R^1$ is hydrogen and $R^2$ is benzyl.

In certain embodiments of formula I or formula II, n is 1, m is 0, p is 0, $R^4$ and $R^5$ are hydrogen, Ar is optionally substituted phenyl, one of $R^1$ and $R^2$ is $C_{1-6}$alkyl, and the other is hydroxy.

In certain embodiments of the invention, the subject compounds are of the formula III:

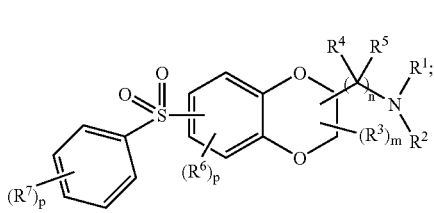

wherein:

n is 1 or 2;

q is from 0 to 4;

each $R^7$ is independently halo, $C_{1-6}$alkyl, halo-$C_{1-6}$alkyl, hetero-$C_{1-6}$alkyl, cyano, —$SO_2R^b$, —C(=O)—$NR^cR^d$, —$SR^c$, —C(=O)—$R^c$, where each of $R^b$, $R^c$ and $R^d$ is independently hydrogen or $C_{1-6}$alkyl; and m, p, $R^1$, $R^2$, $R^3$, $R^4$, $R^5$ and $R^6$ are as defined herein.

In certain embodiments of formula III, $R^4$ and $R^5$ are hydrogen.

In certain embodiments of formula III, m is 0.

In certain embodiments of formula III, n is 1 or 2. Preferably n is 1.

In certain embodiments of formula III, p is 0.

In certain embodiments of formula III, $R^1$ and $R^2$ each independently is hydrogen or $C_{1-6}$alkyl, or $R^1$ and $R^2$ together with the nitrogen to which they are attached form a three, four, five or six-membered ring.

In certain embodiments of formula III, $R^1$ and $R^2$ each independently is hydrogen or $C_{1-6}$alkyl.

In certain embodiments of formula III, $R^1$ and $R^2$ together with the nitrogen to which they are attached form a three, four, five or six-membered ring.

In certain embodiments of formula II, $R^4$ and $R^5$ together form =$NR^f$ wherein $R^f$ is hydrogen or $C_{1-6}$alkyl.

In certain embodiments of formula III, one of $R^1$ and $R^2$ is hydrogen or $C_{1-6}$alkyl and the other is $C_{1-6}$alkylcarbonyl, $C_{3-8}$cycloalkyl, aryl-$C_{1-6}$alkyl, hydroxy, or a five- or six-membered heteroaryl or heterocyclyl that contains one or two nitrogens.

In certain embodiments of formula III, one of $R^4$ and $R^5$ together with one of $R^1$ and $R^2$ and the atoms to which they are attached form a five or six-membered ring.

In certain embodiments of formula III, $R^1$ and $R^2$ together with the nitrogen to which they are attached form a guanidinyl group, an amidinyl group, a carbamyl group, or a urea group. Preferably in such embodiments, $R^1$ and $R^2$ together with the nitrogen to which they are attached form a guanidinyl group.

In certain embodiments of formula III, $R^1$ and $R^2$ together with the nitrogen to which they are attached form a three- to seven-membered ring that optionally contains an additional heteroatom selected from N, O and S.

In certain embodiments of formula III, $R^1$ and $R^2$ together with the nitrogen to which they are attached form a three-membered ring.

In certain embodiments of formula III, $R^1$ and $R^2$ together with the nitrogen to which they are attached form a four-membered ring.

In certain embodiments of formula III, $R^1$ and $R^2$ together with the nitrogen to which they are attached form a five-membered ring.

In certain embodiments of formula III, $R^1$ and $R^2$ together with the nitrogen to which they are attached form a six-membered ring.

In certain embodiments of formula III, m is 1 and $R^3$ is alkyl.

In certain embodiments of formula III, m is 1 and one of $R^1$ and $R^2$ together with $R^3$ and the atoms to which they are attached form a five or six membered ring.

In certain embodiments of formula III, n is 1, m is 0, p is 0, and $R^4$ and $R^5$ are hydrogen.

In certain embodiments of formula III, n is 1, m is 0, p is 0, $R^4$ and $R^5$ are hydrogen, q is from 0 to 2, and $R^7$ is $C_{1-6}$alkyl, halo, halo-$C_{1-6}$alkyl, $C_{1-6}$alkoxy In certain embodiments of formula I or formula II, n is 1, m is 0, p is 0, $R^4$ and $R^5$ are hydrogen, q is from 0 to 2, $R^7$ is $C_{1-6}$alkyl, halo, halo-$C_{1-6}$alkyl, $C_{1-6}$alkoxy, or cyano, and $R^1$ and $R^2$ each independently is hydrogen or $C_{1-6}$alkyl.

In certain embodiments of formula III, n is 1, m is 0, p is 0, $R^4$ and $R^5$ are hydrogen, q is from 0 to 2, $R^7$ is $C_{1-6}$alkyl, halo, halo-$C_{1-6}$alkyl, $C_{1-6}$alkoxy, or cyano, and $R^1$ and $R^2$ together with the nitrogen to which they are attached form a three- to seven-membered ring that optionally contains an additional heteroatom selected from N, O and S.

In certain embodiments of formula III, n is 1, m is 0, p is 0, $R^4$ and $R^5$ are hydrogen, q is from 0 to 2, $R^7$ is $C_{1-6}$alkyl, halo, halo-$C_{1-6}$alkyl, $C_{1-6}$alkoxy, or cyano, and $R^1$ and $R^2$ together with the nitrogen to which they are attached form a guanidinyl group, an amidinyl group, or a urea group. In such embodiments, $R^1$ and $R^2$ together with the nitrogen to which they are attached preferably form a guanidinyl group.

In certain embodiments of formula III, n is 1, m is 0, p is 0, $R^4$ and $R^5$ are hydrogen, q is from 0 to 2, $R^7$ is $C_{1-6}$alkyl, halo, halo-$C_{1-6}$alkyl, $C_{1-6}$alkoxy, or cyano, one of $R^1$ and $R^2$ is hydrogen or $C_{1-6}$alkyl and the other is $C_{1-6}$alkylcarbonyl, $C_{3-8}$cycloalkyl, aryl-$C_{1-6}$alkyl, or a five- or six-membered heteroaryl or heterocyclyl that contains one or two nitrogens. Preferred heteroaryl include imidazolyl, pyrazolyl, pyridyl and pyrimidyl. Preferred heterocyclyl include imidazolinyl, and tetrahydropyrimidinyl.

In certain embodiments of formula III, n is 1, m is 0, p is 0, $R^4$ and $R^5$ are hydrogen, q is from 0 to 2, $R^7$ is $C_{1-6}$alkyl, halo, halo-$C_{1-6}$alkyl, $C_{1-6}$alkoxy, or cyano and $R^2$ is hydrogen or $C_{1-6}$alkyl and the other is $C_{1-6}$alkylcarbonyl. Preferably in such embodiments, $R^1$ is hydrogen and $R^2$ is acetyl.

In certain embodiments of formula III, n is 1, m is 0, p is 0, $R^4$ and $R^5$ are hydrogen, q is from 0 to 2, $R^7$ is $C_{1-6}$alkyl, halo-$C_{1-6}$alkyl, $C_{1-6}$alkoxy, or cyan and $R^2$ is hydrogen or $C_{1-6}$alkyl and the other is $C_{3-8}$cycloalkyl.

In certain embodiments of formula III, n is 1, m is 0, p is 0, $R^4$ and $R^5$ are hydrogen, q is from 0 to 2, $R^7$ is $C_{1-6}$alkyl, halo, halo-$C_{1-6}$alkyl, $C_{1-6}$alkoxy, or cyan and $R^2$ is hydrogen or $C_{1-6}$alkyl and the other is aryl-$C_{1-6}$alkyl. Preferably in such embodiments, $R^1$ is hydrogen and $R^2$ is benzyl.

In certain embodiments of formula III, n is 1, m is 0, p is 0, $R^4$ and $R^5$ are hydrogen, q is from 0 to 2, $R^7$ is $C_{1-6}$alkyl, halo, halo-$C_{1-6}$alkyl, $C_{1-6}$alkoxy, or cyano, one of $R^1$ and $R^2$ is $C_{1-6}$alkyl, and the other is hydroxy.

Compounds of formula III may, in certain embodiments, be more specifically of formula IV:

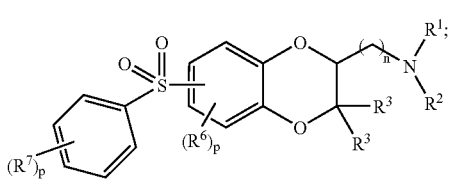

wherein n, p, q, $R^1$, $R^2$, $R^3$, $R^6$ and $R^7$ are as defined herein.

Compounds of formula III may, in certain embodiments, be more specifically of formula V;

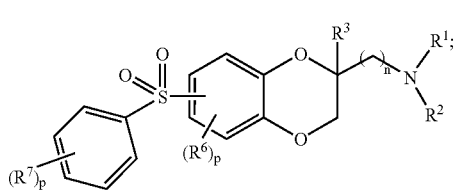

wherein n, p, q, $R^1$, $R^2$, $R^3$, $R^6$ and $R^7$ are as defined herein.

In certain embodiments of formula IV or formula V, n is 1 or 2. Preferably n is 1.

In certain embodiments of formula IV or formula V, p is 0.

In certain embodiments of formula IV or formula V, $R^1$ and $R^2$ each independently is hydrogen or $C_{1-6}$alkyl, or $R^1$ and $R^2$ together with the nitrogen to which they are attached form a three, four, five or six-membered ring.

In certain embodiments of formula IV or formula V, $R^1$ and $R^2$ each independently is hydrogen or $C_{1-6}$alkyl.

In certain embodiments of formula IV or formula V, $R^1$ and $R^2$ together with the nitrogen to which they are attached form a three, four, five or six-membered ring.

In certain embodiments of formula IV or formula V, one of $R^1$ and $R^2$ is hydrogen or $C_{1-6}$alkyl and the other is $C_{1-6}$alkylcarbonyl, $C_{3-8}$cycloalkyl, aryl-$C_{1-6}$alkyl, hydroxy, or a five- or six-membered heteroaryl or heterocyclyl that contains one or two nitrogens.

In certain embodiments of formula IV or formula V, $R^1$ and $R^2$ together with the nitrogen to which they are attached form a guanidinyl group, an amidinyl group, a carbamyl group, or a urea group. Preferably in such embodiments, $R^1$ and $R^2$ together with the nitrogen to which they are attached form a guanidinyl group.

In certain embodiments of formula IV or formula V, $R^1$ and $R^2$ together with the nitrogen to which they are attached form a three- to seven-membered ring that optionally contains an additional heteroatom selected from N, O and S.

In certain embodiments of formula IV or formula V, $R^1$ and $R^2$ together with the nitrogen to which they are attached form a three-membered ring.

In certain embodiments of formula IV or formula V, $R^1$ and $R^2$ together with the nitrogen to which they are attached form a four-membered ring.

In certain embodiments of formula IV or formula V, $R^1$ and $R^2$ together with the nitrogen to which they are attached form a five-membered ring.

In certain embodiments of formula IV or formula V, $R^1$ and $R^2$ together with the nitrogen to which they are attached form a six-membered ring.

In certain embodiments of formula IV or formula V, n is 1 and p is 0.

In certain embodiments of formula IV or formula V, n is 1, p is 0, q is from 0 to 2, and $R^7$ is $C_{1-6}$alkyl, halo, halo-$C_{1-6}$alkyl, $C_{1-6}$alkoxy, or cyano.

In certain embodiments of formula IV or formula V, n is 1, p is 0, q is from 0 to 2, $R^7$ is $C_{1-6}$alkyl, halo, halo-$C_{1-6}$alkyl, $C_{1-6}$alkoxy, or cyano, and $R^1$ and $R^2$ each independently is hydrogen or $C_{1-6}$alkyl.

In certain embodiments of formula IV or formula V, n is 1, p is 0, q is from 0 to 2, $R^7$ is $C_{1-6}$alkyl, halo, halo-$C_{1-6}$alkyl, $C_{1-6}$alkoxy, or cyano, and $R^1$ and $R^2$ together with the nitrogen to which they are attached form a three- to seven-membered ring that optionally contains an additional heteroatom selected from N, O and S.

In certain embodiments of formula IV or formula V, n is 1, p is 0, q is from 0 to 2, $R^7$ is $C_{1-6}$alkyl, halo, halo-$C_{1-6}$alkyl, $C_{1-6}$alkoxy, or cyano, and $R^1$ and $R^2$ together with nitrogen to which they are attached form a guanidinyl group, an amidinyl group, or a urea group. In such embodiments, $R^1$ and $R^2$ together with the nitrogen to which they are attached preferably form a guanidinyl group.

In certain embodiments of formula IV or formula V, n is 1, p is 0, q is from 0 to 2, $R^7$ is $C_{1-6}$alkyl, halo, halo-$C_{1-6}$alkyl, $C_{1-6}$alkoxy, or cyano, one of $R^1$ and $R^2$ is hydrogen or $C_{1-6}$alkyl and the other is $C_{1-6}$alkylcarbonyl, $C_{3-8}$cycloalkyl, aryl-$C_{1-6}$alkyl, or a five- or six-membered heteroaryl or heterocyclyl that contains one or two nitrogens. Preferred heteroaryl include imidazolyl, pyrazolyl, pyridyl and pyrimidyl. Preferred heterocyclyl include imidazolinyl, and tetrahydropyrimidinyl.

In certain embodiments of formula IV or formula V, n is 1, p is 0, q is from 0 to 2, $R^7$ is $C_{1-6}$alkyl, halo, halo-$C_{1-6}$alkyl, $C_{1-6}$alkoxy, or cyano, one of $R^1$ and $R^2$ is hydrogen or $C_{1-6}$alkyl and the other is $C_{1-6}$alkylcarbonyl. Preferably in such embodiments, $R^1$ is hydrogen and $R^2$ is acetyl.

In certain embodiments of formula IV or formula V, n is 1, p is 0, q is from 0 to 2, $R^7$is $C_{1-6}$alkyl, halo, halo-$C_{1-6}$alkyl, $C_{1-6}$alkoxy, or cyano, one of $R^1$ and $R^2$ is hydrogen or $C_{1-6}$alkyl and the other is $C_{3-8}$cycloalkyl.

In certain embodiments of formula IV or formula V, n is 1, p is 0, q is from 0 to 2, $R^7$is $C_{1-6}$alkyl, halo, halo-$C_{1-6}$alkyl, $C_{1-6}$alkoxy, or cyano, one of $R^1$ and $R^2$ is hydrogen or $C_{1-6}$alkyl and the other is aryl-$C_{1-6}$alkyl. Preferably in such embodiments, $R^1$ is hydrogen and $R^2$ is benzyl.

In certain embodiments of formula IV or formula V, n is 1, p is 0, q is from 0 to 2, $R^7$is $C_{1-6}$alkyl, halo, halo-$C_{1-6}$alkyl, $C_{1-6}$alkoxy, or cyano, one of $R^1$ and $R^2$ is $C_{1-6}$alkyl, and the other is hydroxy.

In certain embodiments of formula IV, one of $R^3$ is $C_{1-6}$alkyl and the other is hydrogen.

In certain embodiments of formula IV, both of $R^3$ are hydrogen.

In certain embodiments of formula IV, both of $R^3$ are $C_{1-6}$alkyl.

In certain embodiments of formula IV, both of $R^3$ together with the atoms to which they are attached form a $C_{4-6}$carbocyclic ring.

In certain embodiments of formula V, $R^3$is $C_{1-6}$alkyl.

In certain embodiments of formula V, $R^3$is hydrogen.

In certain embodiments of formula V, $R^3$ together with one of $R^1$ and $R^2$ and the atoms to which they are attached form a five- or six-membered ring. Preferably in such embodiments R³ together with one of R¹ and R² and the atoms to which they are attached form a five-membered ring.

The subject compounds may, in certain embodiments, be of the formula VI:

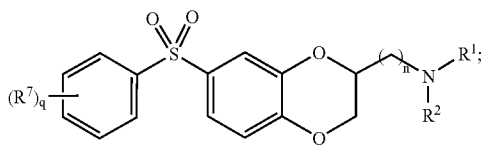

wherein n, q, R¹, R² and R⁷ are as defined herein.

The subject compounds may, in certain embodiments, be of the formula VII:

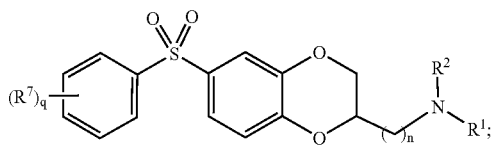

wherein n, q, R¹, R² and R⁷ are as defined herein.

In certain embodiments of formula VI or formula VII, n is 1 or 2. Preferably n is 1.

In certain embodiments of formula VI or formula VII, R¹ and R² each independently is hydrogen or $C_{1-6}$alkyl, or R¹ and R² together with the nitrogen to which they are attached form a three, four, five or six-membered ring.

In certain embodiments of formula VI or formula VII, R¹ and R² each independently is hydrogen or $C_{1-6}$alkyl.

In certain embodiments of formula VI or formula VII, R¹ and R² together with the nitrogen to which they are attached form a three, four, five or six-membered ring.

In certain embodiments of formula VI or formula VII, one of R¹ and R² is hydrogen or $C_{1-6}$alkyl and the other is $C_{1-6}$alkylcarbonyl, $C_{3-8}$cycloalkyl, aryl-$C_{1-6}$alkyl, hydroxy, or a five- or six-membered heteroaryl or heterocyclyl that contains one or two nitrogens.

In certain embodiments of formula IV or formula V, R¹ and R² together with the nitrogen to which they are attached form a guanidinyl group, an amidinyl group, a carbamyl group, or a urea group. Preferably in such embodiments, R¹ and R² together with the nitrogen to which they are attached form a guanidinyl group.

In certain embodiments of formula VI or formula VII, R¹ and R² together with the nitrogen to which they are attached form a three- to seven-membered ring that optionally contains an additional heteroatom selected from N, O and S.

In certain embodiments of formula VI or formula VII, R¹ and R² together with the nitrogen to which they are attached form a three-membered ring.

In certain embodiments of formula VI or formula VII, R¹ and R² together with the nitrogen to which they are attached form a four-membered ring.

In certain embodiments of formula VI or formula VII, R¹ and R² together with the nitrogen to which they are attached form a five-membered ring.

In certain embodiments of formula VI or formula VII, R¹ and R² together with the nitrogen to which they are attached form a six-membered ring.

In certain embodiments of formula VI or formula VII, n is 1, q is from 0 to 2, and R⁷ is $C_{1-6}$alkyl, halo, halo-$C_{1-6}$alkyl, $C_{1-6}$alkoxy, or cyano.

In certain embodiments of formula VI or formula VII, n is 1, q is from 0 to 2, R⁷ is $C_{1-6}$alkyl, halo, halo-$C_{1-6}$alkyl, $C_{1-6}$alkoxy, or cyano, and R¹ and R² each independently is hydrogen or $C_{1-6}$alkyl.

In certain embodiments of formula VI or formula VII, n is 1, q is from 0 to 2, R⁷ is $C_{1-6}$alkyl, halo, halo-$C_{1-6}$alkyl, $C_{1-6}$alkoxy, or cyano, and R¹ and R² together with the nitrogen to which they are attached form a three- to seven-membered ring that optionally contains an additional heteroatom selected from N, O and S.

In certain embodiments of formula VI or formula VII, n is 1, q is from 0 to 2, R⁷ is $C_{1-6}$alkyl, halo, halo-$C_{1-6}$alkyl, $C_{1-6}$alkoxy, or cyano, and R¹ and R² together with the nitrogen to which they are attached form a guanidinyl group, an amidinyl group, or a urea group. In such embodiments, R¹ and R² together with the nitrogen to which they are attached preferably form a guanidinyl group.

In certain embodiments of formula VI or formula VII, n is 1, q is from 0 to 2, R⁷ is $C_{1-6}$alkyl, halo, halo-$C_{1-6}$alkyl, $C_{1-6}$alkoxy, or cyano, one of R¹ and R² is hydrogen or $C_{1-6}$alkyl and the other is $C_{1-6}$alkylcarbonyl, $C_{3-8}$cycloalkyl, aryl-$C_{1-6}$alkyl, or a five- or six-membered heteroaryl or heterocyclyl that contains one or two nitrogens. Preferred heteroaryl include imidazolyl, pyrazolyl, pyridyl and pyrimidyl. Preferred heterocyclyl include imidazolinyl, and tetrahydropyrimidinyl.

In certain embodiments of formula VI or formula VII, n is 1, q is from 0 to 2, R⁷ is $C_{1-6}$alkyl, halo, halo-$C_{1-6}$alkyl, $C_{1-6}$alkoxy, or cyano, one of R¹ and R² is hydrogen or $C_{1-6}$alkyl and the other is $C_{1-6}$alkylcarbonyl. Preferably in such embodiments, R¹ is hydrogen and R² is acetyl.

In certain embodiments of formula VI or formula VII, n is 1, q is from 0 to 2, R⁷ is $C_{1-6}$alkyl, halo, halo-$C_{1-6}$alkyl, $C_{1-6}$alkoxy, or cyano, one of R¹ and R² is hydrogen or $C_{1-6}$ alkyl and the other is $C_{3-8}$cycloalkyl.

In certain embodiments of formula VI or formula VII, n is 1, q is from 0 to 2, R⁷ is $C_{1-6}$alkyl, halo, halo-$C_{1-6}$alkyl, $C_{1-6}$alkoxy, or cyano, one of R¹ and R² is hydrogen or $C_{1-6}$ alkyl and the other is aryl-$C_{1-6}$alkyl. Preferably in such embodiments, R¹ is hydrogen and R² is benzyl.

In certain embodiments of formula VI or formula VII, n is 1, q is from 0 to 2, R⁷ is $C_{1-6}$alkyl, halo, halo-$C_{1-6}$alkyl, $C_{1-6}$alkoxy, or cyano, one of R¹ and R² is $C_{1-6}$alkyl, and the other is hydroxy.

The subject compounds may, in certain embodiments, be of the formula VIII:

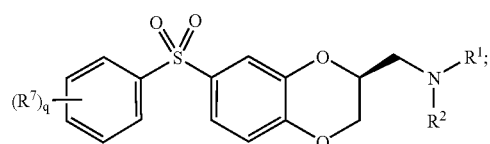

wherein q, R¹, R² and R⁷ are as defined herein.

The subject compounds may, in certain embodiments, be of the formula IX:

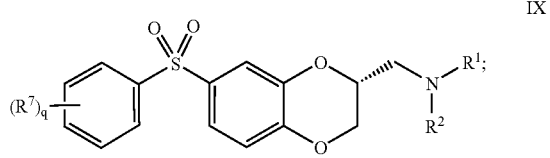

IX wherein q, $R^1$, $R^2$ and $R^7$ are as defined herein.

In certain embodiments of formula VIII or formula IX, $R^1$ and $R^2$ each independently is hydrogen or $C_{1-6}$alkyl, or $R^1$ and $R^2$ together with the nitrogen to which they are attached form a three, four, five or six-membered ring.

In certain embodiments of formula VIII or formula IX, $R^1$ and $R^2$ each independently is hydrogen or $C_{1-6}$alkyl.

In certain embodiments of formula VIII or formula IX, $R^1$ and $R^2$ together with the nitrogen to which they are attached form a three, four, five or six-membered ring.

In certain embodiments of formula VIII or formula IX, one of $R^1$ and $R^2$ is hydrogen or $C_{1-6}$alkyl and the other is $C_{1-6}$alkylcarbonyl, $C_{3-8}$cycloalkyl, aryl-$C_{1-6}$alkyl, hydroxy, or a five- or six-membered heteroaryl or heterocyclyl that contains one or two nitrogens.

In certain embodiments of formula VIII or formula IX, $R^1$ and $R^2$ together with the nitrogen to which they are attached form a guanidinyl group, an amidinyl group, a carbamyl group, or a urea group. Preferably in such embodiments, $R^1$ and $R^2$ together with the nitrogen to which they are attached form a guanidinyl group.

In certain embodiments of formula VIII or formula IX, $R^1$ and $R^2$ together with the nitrogen to which they are attached form a three- to seven-membered ring that optionally contains an additional heteroatom selected from N, O and S.

In certain embodiments of formula VIII or formula IX, $R^1$ and $R^2$ together with the nitrogen to which they are attached form a three-membered ring.

In certain embodiments of formula VIII or formula IX, $R^1$ and $R^2$ together with the nitrogen to which they are attached form a four-membered ring.

In certain embodiments of formula VIII or formula IX, $R^1$ and $R^2$ together with the nitrogen to which they are attached form a five-membered ring.

In certain embodiments of formula VIII or formula IX, $R^1$ and $R^2$ together with the nitrogen to which they are attached form a six-membered ring.

In certain embodiments of formula VIII or formula IX, q is from 0 to 2, and $R^7$ is $C_{1-6}$alkyl, halo, halo-$C_{1-6}$alkyl, $C_{1-6}$alkoxy, or cyano.

In certain embodiments of formula VIII or formula IX, q is from 0 to 2, $R^7$ is $C_{1-6}$alkyl, halo, halo-$C_{1-6}$alkyl, $C_{1-6}$alkoxy, or cyano, and $R^1$ and $R^2$ each independently is hydrogen or $C_{1-6}$alkyl.

In certain embodiments of formula VIII or formula IX, q is from 0 to 2, $R^7$ is $C_{1-6}$alkyl, halo, halo-$C_{1-6}$alkyl, $C_{1-6}$alkoxy, or cyano, and $R^1$ and $R^2$ together with the nitrogen to which they are attached form a three- to seven-membered ring that optionally contains an additional heteroatom selected from N, O and S.

In certain embodiments of formula VIII or formula IX, q is from 0 to 2, $R^7$ is $C_{1-6}$alkyl, halo, halo-$C_{1-6}$alkyl, $C_{1-6}$alkoxy, or cyano, and $R^1$ and $R^2$ together with the nitrogen to which they are attached form a guanidinyl group, an amidinyl group, or a urea group. In such embodiments, $R^1$ and $R^2$ together with the nitrogen to which they are attached preferably form a guanidinyl group.

In certain embodiments of formula VIII or formula IX, p is 0, q is from 0 to 2, $R^7$ is $C_{1-6}$alkyl, halo, halo-$C_{1-6}$alkyl, $C_{1-6}$alkoxy, or cyano, one of $R^1$ and $R^2$ is hydrogen or $C_{1-6}$alkyl and the other is $C_{1-6}$alkylcarbonyl, $C_{3-8}$cycloalkyl, aryl-$C_{1-6}$alkyl, or a five- or six-membered heteroaryl or heterocyclyl that contains one or two nitrogens. Preferred heteroaryl include imidazolyl, pyrazolyl, pyridyl and pyrimidyl. Preferred heterocyclyl include imidazolinyl, and tetrahydropyrimidinyl.

In certain embodiments of formula VIII or formula IX, q is from 0 to 2, $R^7$ is $C_{1-6}$alkyl, halo, halo-$C_{1-6}$alkyl, $C_{1-6}$alkoxy, or cyano, one of $R^1$ and $R^2$ is hydrogen or $C_{1-6}$alkyl and the other is $C_{1-6}$alkylcarbonyl. Preferably in such embodiments, $R^1$ is hydrogen and $R^2$ is acetyl.

In certain embodiments of formula VIII or formula IX, n is 1, p is 0, q is from 0 to 2, $R^7$ is $C_{1-6}$alkyl, halo, halo-$C_{1-6}$alkyl, $C_{1-6}$alkoxy, or cyano, one of $R^1$ and $R^2$ is hydrogen or $C_{1-6}$alkyl and the other is $C_{3-8}$cycloalkyl.

In certain embodiments of formula VIII or formula IX, q is from 0 to 2, $R^7$ is $C_{1-6}$alkyl, halo, halo-$C_{1-6}$alkyl, $C_{1-6}$alkoxy, or cyano, one of $R^1$ and $R^2$ is hydrogen or $C_{1-6}$alkyl and the other is aryl-$C_{1-6}$alkyl. Preferably in such embodiments, $R^1$ is hydrogen and $R^2$ is benzyl.

In certain embodiments of formula VIII or formula IX, q is from 0 to 2, $R^7$ is $C_{1-6}$alkyl, halo, halo-$C_{1-6}$alkyl, $C_{1-6}$alkoxy, or cyano, one of $R^1$ and $R^2$ is $C_{1-6}$alkyl, and the other is hydroxy.

In certain embodiments of formula VIII, q is 0 or 1, $R^7$ is halo, one of $R^1$ and $R^2$ is $C_{1-6}$alkyl, and the other is hydrogen.

Where any of $R^1$, $R^2$, $R^3$, $R^4$, $R^5$, $R^6$ or $R^7$ are alkyl or contain an alkyl moiety, such alkyl is preferably lower alkyl, i.e. $C_1$-$C_6$alkyl, and more preferably $C_1$-$C_4$alkyl.

Representative compounds in accordance with the methods of the invention are shown in Table 1. Melting points shown in Table 1 represent the corresponding hydrochloride salts unless indicated otherwise.

TABLE 1

| # | Structure | Name (Autonom ™) | Mp ° C. |
|---|-----------|------------------|---------|
| 1 | 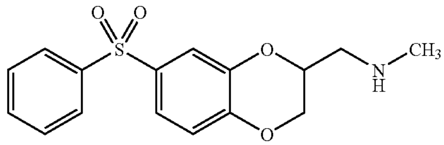 | (+−)-(7-Benzenesulfonyl-2,3-dihydro-benzo[1,4]dioxin-2-ylmethyl)-methyl-amine | 198.0-199.4 |

TABLE 1-continued

| # | Structure | Name (Autonom ™) | Mp ° C. |
|---|---|---|---|
| 2 | 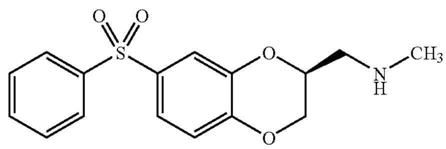 | (7-Benzenesulfonyl-2,3-dihydro-benzo[1,4]dioxin-2--(S)-ylmethyl)-methyl-amine | 240.0-243.6 |
| 3 | 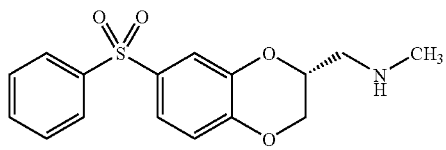 | (7-Benzenesulfonyl-2,3-dihydro-benzo[1,4]dioxin-2-(R)-ylmethyl)-methyl-amine | 247.1-249.9 |
| 4 | 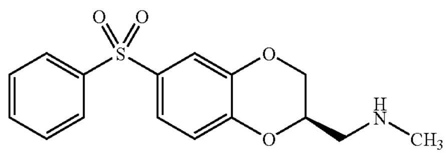 | (6-Benzenesulfonyl-2,3-dihydro-benzo[1,4]dioxin-2-(R)-ylmethyl)-methyl-amine | 219.7-225.4 |
| 5 | 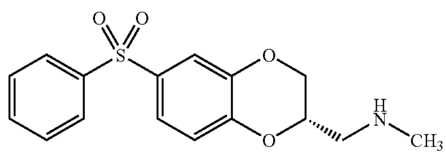 | (6-Benzenesulfonyl-2,3-dihydro-benzo[1,4]dioxin-2-(S)-ylmethyl)-methyl-amine | 218.2-220.5 |
| 6 | 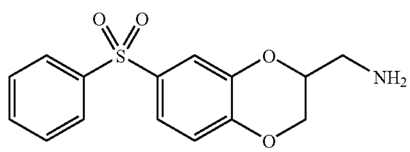 | (7-Benzenesulfonyl-2,3-dihydro-benzo[1,4]dioxin-2-yl)-methylamine | 107.8-111.9 |
| 7 | 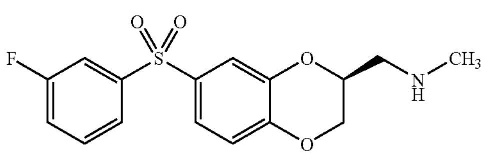 | [7-(3-Fluoro-benzenesulfonyl)-2,3-dihydro-benzo[1,4]dioxin-2-(S)-ylmethyl]-methyl-amine | 245.8-246.4 |
| 8 | 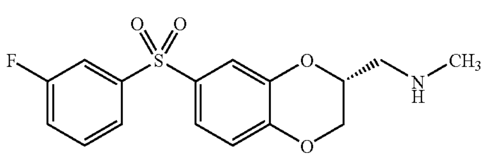 | [7-(3-Fluoro-benzenesulfonyl)-2,3-dihydro-benzo[1,4]dioxin-2-(R)-ylmethyl]-methyl-amine | 250.1-254.3 |
| 9 | 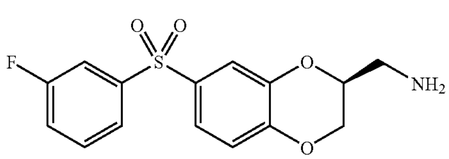 | C-[7-(3-Fluoro-benzenesulfonyl)-2,3-dihydro-benzo[1,4]dioxin-2-(S)-yl]-methylamine | 224.9-227.9 |
| 10 | 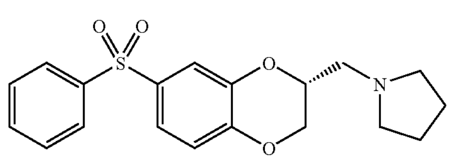 | 1-(7-Benzenesulfonyl-2,3-dihydro-benzol[1,4]dioxin-2-(R)-ylmethyl)-pyrrolidine | 75.8-112.7 |

TABLE 1-continued

| # | Structure | Name (Autonom ™) | Mp ° C. |
|---|---|---|---|
| 11 | 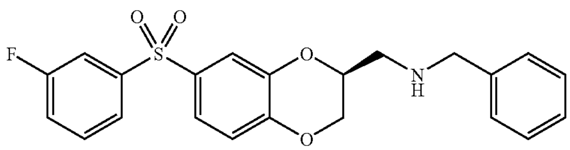 | Benzyl-[7-(3-fluoro-benzenesulfonyl)-2,3-dihydro-benzo[1,4]dioxin-2-ylmethyl]-amine | 195.1-197.1 |
| 12 | 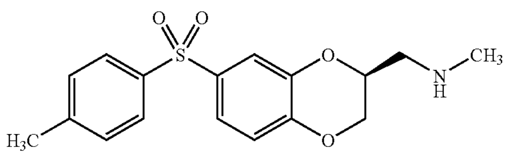 | Methyl-[7-(toluene-4-sulfonyl)-2,3-dihydro-benzo[1,4]dioxin-2-ylmethyl]-amine | 213.0-214.1 |
| 13 | 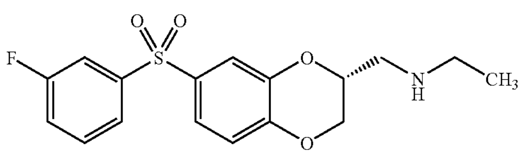 | Ethyl-[7-(3-fluoro-benzenesulfonyl)-2,3-dihydro-benzo[1,4]dioxin-2-ylmethyl]-amine | 247.5-251.3 |
| 14 | 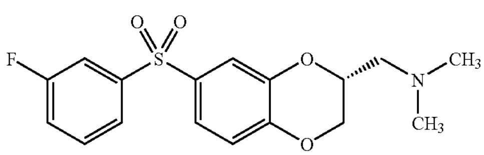 | [7-(3-Fluoro-benzenesulfonyl)-2,3-dihydro-benzo[1,4]dioxin-2-ylmethyl]-dimethyl-amine | 228.7-231.3 |
| 15 | 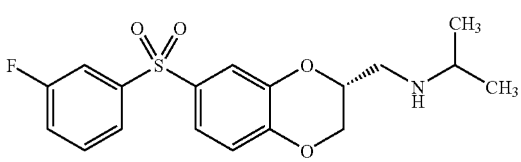 | [7-(3-Fluoro-benzenesulfonyl)-2,3-dihydro-benzo[1,4]dioxin-2-ylmethyl]-isopropyl-amine | 242.4-243.8 |
| 16 | 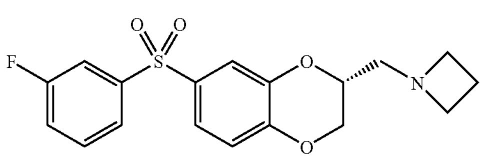 | 1-[7-(3-Fluoro-benzenesulfonyl)-2,3-dihydro-benzo[1,4]dioxin-2-ylmethyl]-azetidine | 100.8-108.3 |
| 17 | 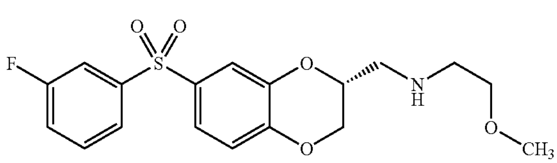 | [7-(3-Fluoro-benzenesulfonyl)-2,3-dihydro-benzo[1,4]dioxin-2-ylmethyl]-(2-methoxy-ethyl)-amine | 193.0-196.9 |
| 18 | 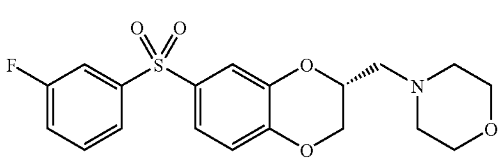 | 4-[7-(3-Fluoro-benzenesulfonyl)-2,3-dihydro-benzo[1,4]dioxin-2-ylmethyl]-morpholine | |
| 19 | 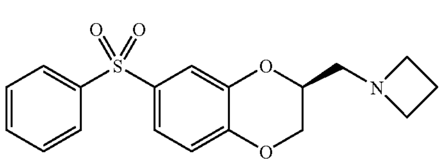 | 1-(7-Benzenesulfonyl-2,3-dihydro-benzo[1,4]dioxin-2-ylmethyl)-azetidine | 132.3-135.5 |

TABLE 1-continued

| # | Structure | Name (Autonom ™) | Mp ° C. |
|---|---|---|---|
| 20 | 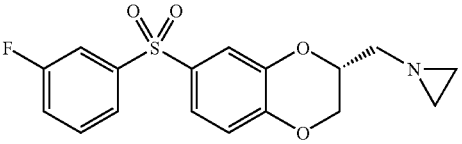 | 1-[7-(3-Fluoro-benzenesulfonyl)-2,3-dihydro-benzo[1,4]dioxin-2-ylmethyl]-aziridine | 215.4-217.2 |
| 21 | 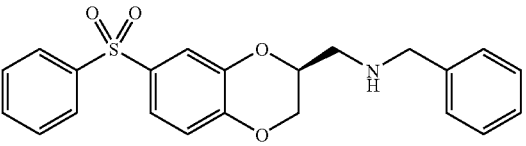 | (7-Benzenesulfonyl-2,3-dihydro-benzo[1,4]dioxin-2-ylmethyl)-benzyl-amine | 220.9-224.9 |
| 22 | 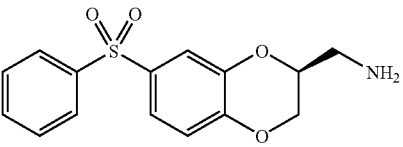 | C-(7-Benzenesulfonyl-2,3-dihydro-benzo[1,4]dioxin-2-yl)-methylamine | |
| 23 | 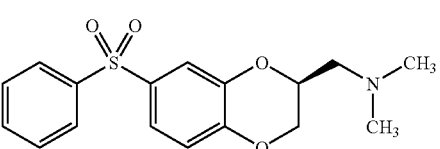 | (7-Benzenesulfonyl-2,3-dihydro-benzo[1,4]dioxin-2-ylmethyl)-dimethyl-amine | 232.0-233.5 |
| 24 | 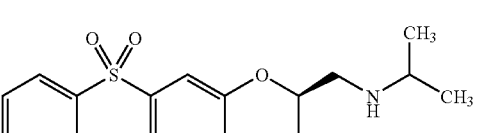 | (7-Benzenesulfonyl-2,3-dihydro-benzo[1,4]dioxin-2-ylmethyl)-isopropyl-amine | 224.9-228.8 |
| 25 | 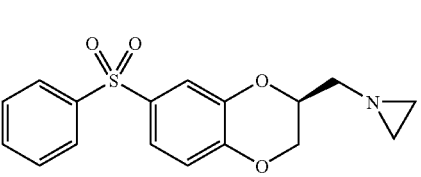 | 1-(7-Benzenesulfonyl-2,3-dihydro-benzo[1,4]dioxin-2-ylmethyl)-aziridine | 203.9-206.6 |
| 26 | 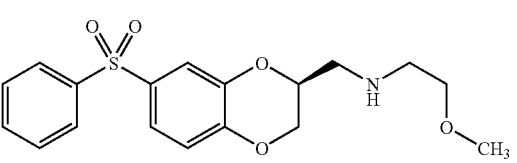 | (7-Benzenesulfonyl-2,3-dihydro-benzo[1,4]dioxin-2-ylmethyl)-(2-methoxy-ethyl)-amine | 169.3-171.9 |
| 27 | 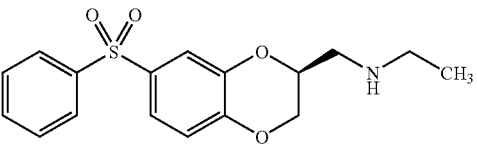 | (7-Benzenesulfonyl-2,3-dihydro-benzo[1,4]dioxin-2-ylmethyl)-ethyl-amine | 242.2-246.7 |
| 28 | 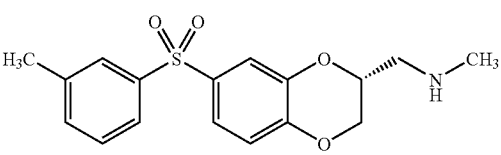 | Methyl-[7-(toluene-3-sulfonyl)-2,3-dihydro-benzo[1,4]dioxin-2-ylmethyl]-amine | 99.9-106.1 |

TABLE 1-continued

| # | Name (Autonom ™) | Mp ° C. |
|---|---|---|
| 29 | Methyl-[7-(toluene-2-sulfonyl)-2,3-dihydro-benzo[1,4]dioxin-2-ylmethyl]-amine | 169.0-170.8 |
| 30 | 1-(7-Benzenesulfonyl-2,3-dihydro-benzo[1,4]dioxin-2-ylmethyl)-piperazine | 279.2-279.4 |
| 31 | N-(7-Benzenesulfonyl-2,3-dihydro-benzo[1,4]dioxin-2-ylmethyl)-guanidine | 126.5-128.3 |
| 32 | 7-Benzenesulfonyl-2,3-dihydro-benzo[1,4]dioxin-2,2'-spiro-3-pyrrolidine | |
| 33 | N-(7-Benzenesulfonyl-2,3-dihydro-benzo[1,4]dioxin-2-ylmethyl)-N-methyl hydroxylamine | 199.2-200.8 |
| 34 | 1-(7-Benzenesulfonyl-2,3-dihydro-benzo[1,4]dioxin-2-ylmethyl)-1H-imidazole | 88.0-90.0 |
| 35 | N-(7-Benzenesulfonyl-2,3-dihydro-benzo[1,4]dioxin-2-ylmethyl)-acetamide | |
| 36 | 2-(3-Methylaminomethyl-2,3-dihydro-benzo[1,4]dioxine-6-sulfonyl)-benzonitrile | |
| 37 | 1-(7-Benzenesulfonyl-2,3-dihydro-benzo[1,4]dioxin-2-ylmethyl)-pyrrolidin-3-ol | 94.7-96.4 |

TABLE 1-continued

| # | Structure | Name (Autonom ™) | Mp ° C. |
|---|---|---|---|
| 38 | 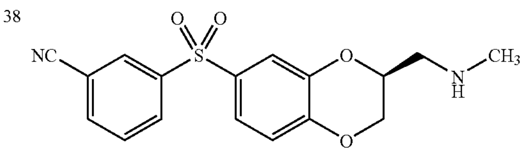 | 3-(3-Methylaminomethyl-2,3-dihydro-benzo[1,4]dioxine-6-sulfonyl)-benzonitrile | 190.6-192.1 |
| 39 | 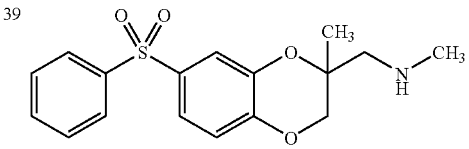 | (7-Benzenesulfonyl-2-methyl-2,3-dihydro-benzo[1,4]dioxin-2-ylmethyl)-methyl-amine | |
| 40 | 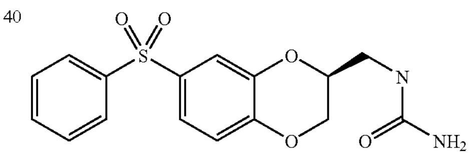 | (7-Benzenesulfonyl-2,3-dihydro-benzo[1,4]dioxin-2-ylmethyl)-urea | 104.9-105.7 |
| 41 | (3:2) | [2-(6-Benzenesulfonyl-2,3-dihydro-benzo[1,4]dioxin-2-yl)-ethyl]-methyl-amine and [2-(7-Benzenesulfonyl-2,3-dihydro-benzo[1,4]dioxin-2-yl)-ethyl]-methyl-amine | |

Synthesis

Compounds of the present invention can be made by a variety of methods depicted in the illustrative synthetic reaction schemes shown and described below.

The starting materials and reagents used in preparing these compounds generally are either available from commercial suppliers, such as Aldrich Chemical Co., or are prepared by methods known to those skilled in the art following procedures set forth in references such as *Fieser and Fieser's Reagents for Organic Synthesis*; Wiley & Sons: New York, 1991, Volumes 1-15; *Rodd's Chemistry of Carbon Compounds*, Elsevier Science Publishers, 1989, Volumes 1-5 and Supplementals; and *Organic Reactions*, Wiley & Sons: New York, 1991, Volumes 1-40. The following synthetic reaction schemes are merely illustrative of some methods by which the compounds of the present invention can be synthesized, and various modifications to these synthetic reaction schemes can be made and will be suggested to one skilled in the art having referred to the disclosure contained in this Application.

The starting materials and the intermediates of the synthetic reaction schemes can be isolated and purified if desired using conventional techniques, including but not limited to, filtration, distillation, crystallization, chromatography, and the like. Such materials can be characterized using conventional means, including physical constants and spectral data.

Unless specified to the contrary, the reactions described herein preferably are conducted under an inert atmosphere at atmospheric pressure at a reaction temperature range of from about −78° C. to about 150° C., more preferably from about 0° C. to about 125° C., and most preferably and conveniently at about room (or ambient) temperature, e.g., about 20° C.

Scheme A below illustrates one synthetic procedure usable to prepare compounds of the invention, wherein n, X, Ar, $R^1$, $R^2$, $R^3$, $R^4$, $R^5$ and $R^6$ are as defined herein.

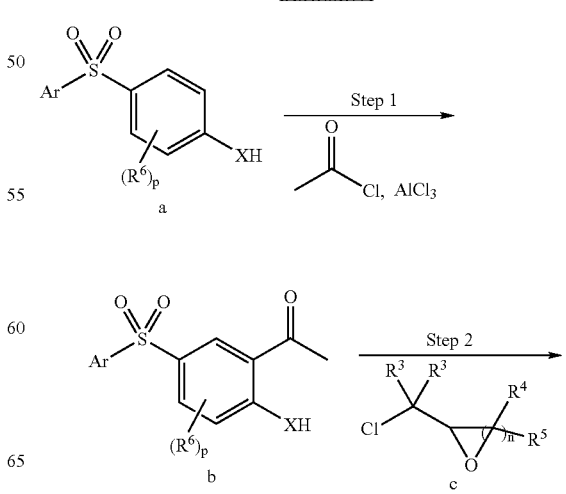

SCHEME A

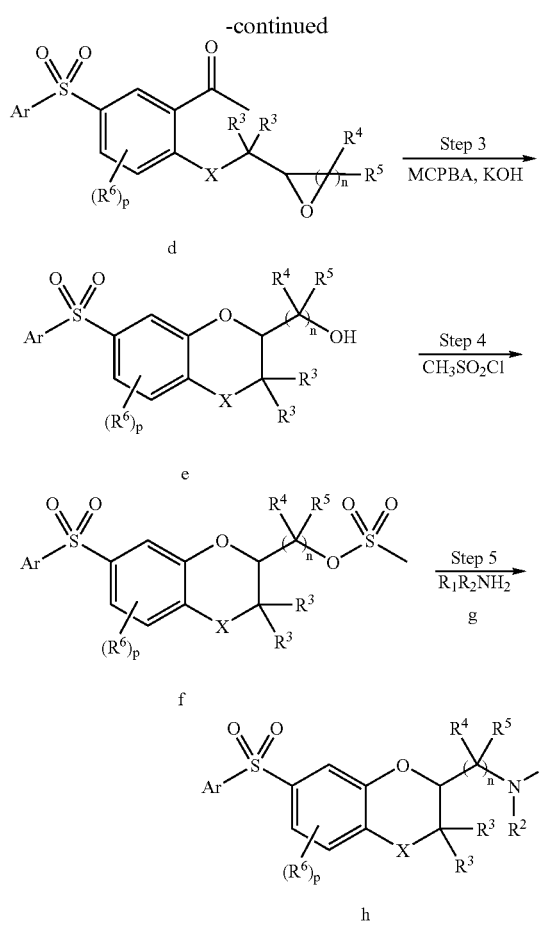

step 5 may be achieved under polar aprotic solvent conditions in the presence of a trialkylamine catalyst.

In step 5, mesylate compound f is reacted with an amine g to afford compound h. This reaction may be carried out under polar protic solvent conditions with heating. Compound h is a compound of formula I in accordance with the invention.

The procedure of Scheme A provides compounds in accordance with the invention wherein an arylsulfonyl group and an aminoalkyl group are placed in a "meta" relationship with respect to the core benzodioxane (or benzoxazine or benzothiazine) ring system. In other words, an arylsulfonyl group is placed at the 7-position, and an aminoalkyl group is placed at the 2-position, of the core ring system. As noted above, compound h may be enantomerically pure with respect to stereochemistry at the 2-position of the ring system when made by the above procedure.

Many variations are possible in the procedure of Scheme A. For example, amine g in step 5 may be a cyclic amine wherein $R^1$ and $R^2$ form a ring. A cyanate may be used in stead of amine g to react with the mesylate f to afford, after reduction of the cyano group and necessary alkylation, compounds of formula I with n=2. Other variations will suggest themselves to those skilled in the art.

The procedure of Scheme A above results in a compound h having the same stereochemistry with respect to that of halomethyl oxirane c.

Scheme B below illustrates another synthetic procedure that may be used in preparation of compounds of the invention, wherein the stereochemistry of the starting materials is preserved in the final product. In Scheme B, p, Ar, $R^1$, $R^2$, $R^3$, $R^4$, $R^5$ and $R^6$ again are as defined herein.

SCHEME B

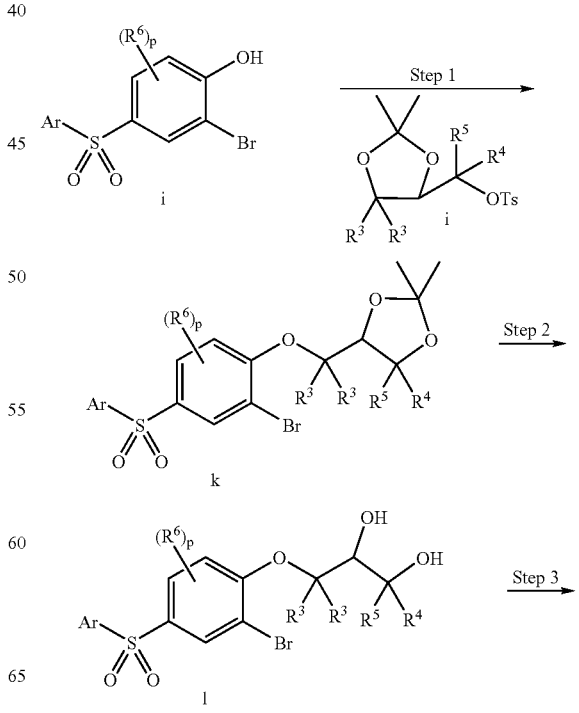

In Step 1 of Scheme A, arylsulfonyl compound a is treated with acetyl chloride or like acyl halide, in the presence of a Lewis acid such as aluminum trichloride, to provide an acyl arylsulfonyl compound b. As noted above, X may be O, S or $NR^a$, such that arylsulfonyl compound a may be a phenol, thiophenol or aniline compound. In embodiments wherein X is $NR^a$ and $R^a$ is hydrogen, conventional amine protecting group techniques may be used. Arylsulfonyl compound a may be prepared by reaction of an arylsulfonyl halide or heteroarylsulfonyl halide with a suitably protected phenol (where X is O), thiophenol (where X is S) or aniline (where X is $NR^a$), followed by deprotection. One such preparation of an arylsulfonyl compound a is described by Sung-Eun et al. in EP 0 514 935 B1.

In step 2, acyl arylsulfonyl compound b undergoes an alkylation reaction with a haloalkyl cyclic oxide such as halomethyl oxirane c to yield an arylsulfonyl methylloxirane ether compound d. This reaction may be carried out in the presence of mild base under polar solvent conditions.

A Bayer-Villager oxidation is carried out in step 3 by treating compound d with a peracid such as meta-chloro perbenzoic acid (MCPBA) or other peracid to form an aryl sulfonyl acetate intermediate (not shown), which is treated with base such as potassium hydroxide to effect a cyclization and afford alcohol compound e. Compound e may be a benzodioxane where X is O, a benzothiazine where X is S, or a benzoxazine where X is $NR^a$.

A mesylate compound f is formed in step 4 by treatment of alcohol e with methane sulfonyl chloride. The reaction of

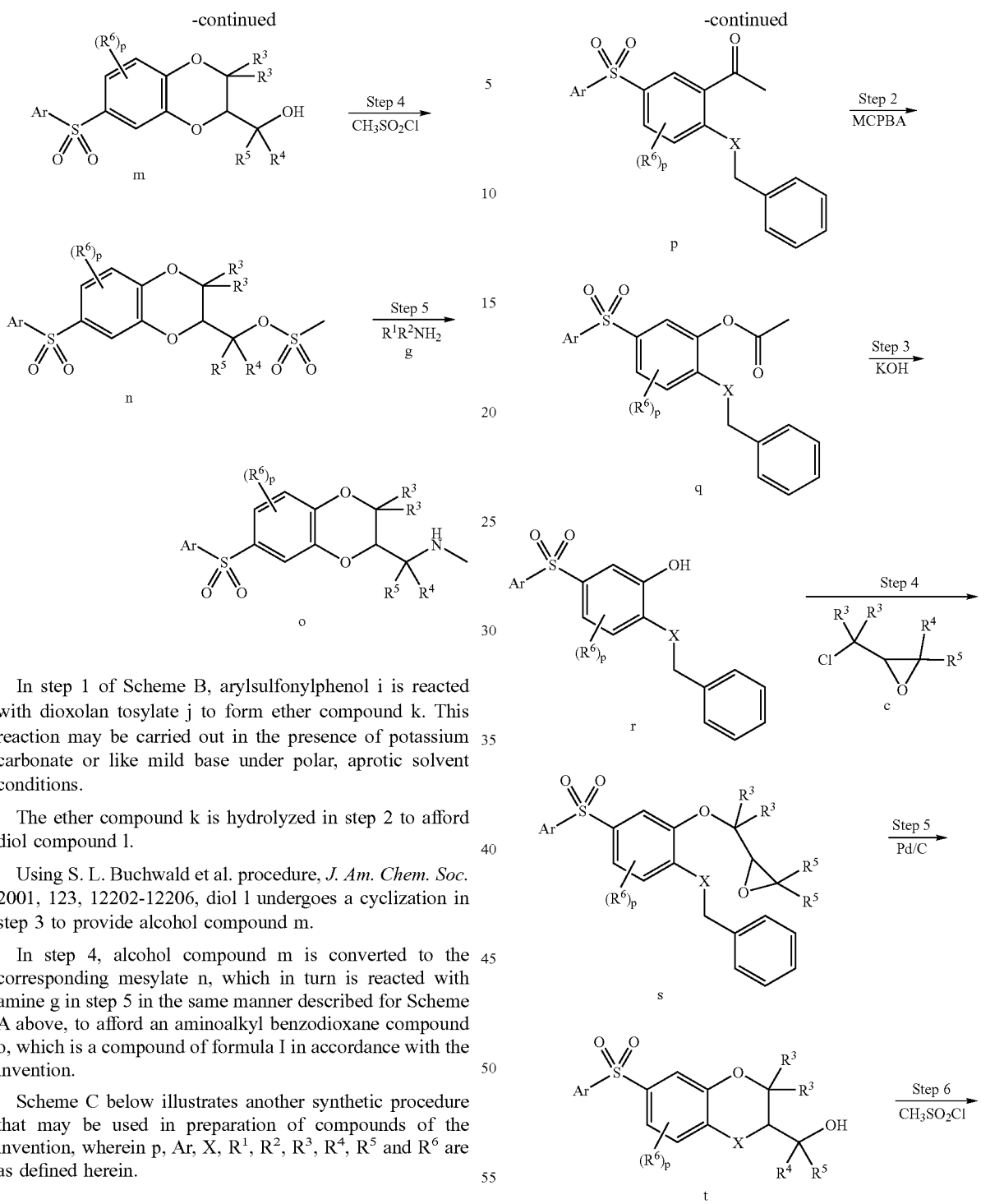

In step 1 of Scheme B, arylsulfonylphenol i is reacted with dioxolan tosylate j to form ether compound k. This reaction may be carried out in the presence of potassium carbonate or like mild base under polar, aprotic solvent conditions.

The ether compound k is hydrolyzed in step 2 to afford diol compound l.

Using S. L. Buchwald et al. procedure, *J. Am. Chem. Soc.* 2001, 123, 12202-12206, diol l undergoes a cyclization in step 3 to provide alcohol compound m.

In step 4, alcohol compound m is converted to the corresponding mesylate n, which in turn is reacted with amine g in step 5 in the same manner described for Scheme A above, to afford an aminoalkyl benzodioxane compound o, which is a compound of formula I in accordance with the invention.

Scheme C below illustrates another synthetic procedure that may be used in preparation of compounds of the invention, wherein p, Ar, X, $R^1$, $R^2$, $R^3$, $R^4$, $R^5$ and $R^6$ are as defined herein.

SCHEME C

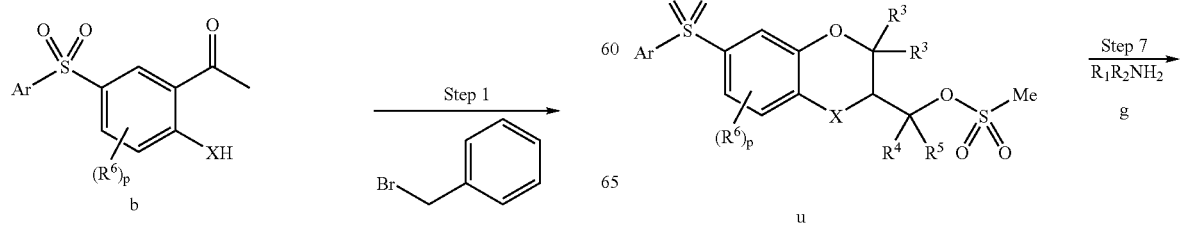

SCHEME D

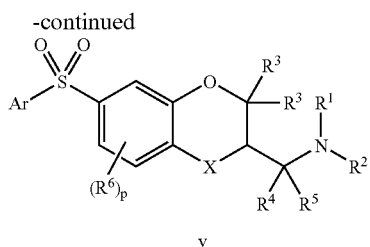

v

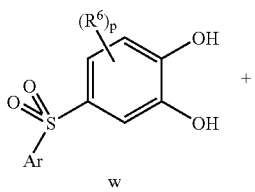

w

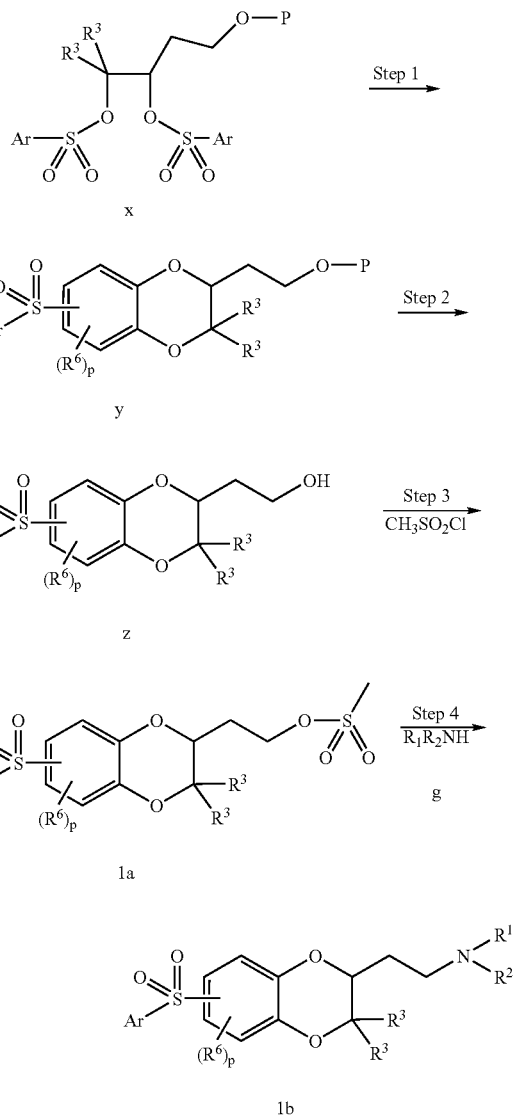

In step 1 of Scheme B, arylsulfonyl compound b is alkylated with benzyl bromide to provide a benzyl ether compound p. As indicated above, in embodiments wherein X is $NR^a$, suitable amine protecting group techniques may be employed in this step and other steps.

In step 2, a Bayer-Villager oxidation is carried out by treating compound p with a peracid in the manner described for step 3 of Scheme A, to form acetate compound q.

Acetate compound q is subject to base-catalyzed hydrolysis in step 3 to remove the acetate group from compound q and provide phenolic compound r.

In step 4, alkylation of compound r with a haloalkyl cyclic oxide such as halomethyl oxirane c, is carried out in the manner described for step 2 of Scheme A above, to yield a methylloxirane ether s.

A cyclization is carried out in step 5 by debenzylation of s to form a phenol intermediate (not shown), which then undergoes cyclization to give alcohol compound t. Compound t may be a benzodioxane where X is O, a benzoxathian where X is S, or a benzoxazine where X is $NR^a$. As in the case of Scheme A above, the cyclization reaction of step 5 of Scheme B preserves stereochemistry (not shown) associated with halomethyl oxirane c, such that enantomerically pure product with respect to the 2-position of the ring system compound t is provided.

In step 6 a mesylate compound u is formed by reaction of alcohol compound t with methane sulfonyl chloride, in the manner described above for step 5 of Scheme A.

In step 7 of Scheme B, mesylate compound u is reacted with an amine g to afford compound v in the manner described for step 5 of Scheme A above. Compound v is a compound of formula I in accordance with the invention, and can be enantiomerically pure with respect to stereochemistry at the 2-position of the ring system as related above. Alternatively, mesylate compound u may be reacted with a cyanate to afford, after subsequent reduction and alkylation, compounds of formula I with n=2.

Many variations are possible in the procedure of Scheme C and will suggest themselves to those skilled in the art.

Scheme D below illustrates yet another synthetic procedure that may be used in preparation of compounds of the invention, wherein p, Ar, X, $R^1$, $R^2$, $R^3$ and $R^6$ are as defined herein. In this Scheme Ar may be the same or different in each occurrence.

In step 1 of Scheme D, arylsulfonylcatechol compound w is alkylated with a diarylsulfonate x, such as a ditosylate, to give benzodioxane y. Benzodioxane y may be a mixture of regioisomers which may separated in this step or s subsequent step, or used together without separation. In step 2, the protecting group P is removed from benzodioxane y to give alcohol z. In step 3, alcohol compound z is converted to the corresponding mesylate 1a by reaction with methanesulfonyl chloride or like alkylsulfonyl halide in the manner described above. Mesylate 1a in turn is reacted with amine g in step 4 in the same manner described for Scheme A above, to afford an aminoalkyl benzodioxane compound 1b which is a compound of formula I in accordance with the invention.

Many variations are possible in the procedure of Scheme D and will suggest themselves to those skilled in the art.

Specific details for producing compounds of the invention are described in the Examples section below.

Utility

The compounds of the invention have selective affinity for 5-HT receptors, including the $5\text{-HT}_6$ the $5\text{-HT}_{2A}$ receptor, or both, and as such are expected to be useful in the treatment of certain CNS disorders such as Parkinson's disease, Huntington's disease, anxiety, depression, manic depression, psychosis, epilepsy, obsessive compulsive disorders, mood disorders, migraine, Alzheimer's disease (enhancement of cognitive memory), sleep disorders, feeding disorders such as anorexia, bulimia, and obesity, panic attacks, akathisia, attention deficit hyperactivity disorder (ADHD), attention deficit disorder (ADD), withdrawal from drug abuse such as cocaine, ethanol, nicotine and benzodiazepines, schizophrenia, and also disorders associated with spinal trauma and/or head injury such as hydrocephalus. Such compounds are also expected to be of use in the treatment of certain GI (gastrointestinal) disorders such functional bowel disorder and irritable bowel syndrome.

Testing

The pharmacology of the compounds of this invention was determined by art recognized procedures. The in vitro techniques for determining the affinities of test compounds at the 5-HT6 receptor and the 5-HT2A receptor in radioligand binding and functional assays are described below.

Administration and Pharmaceutical Composition

The invention includes pharmaceutical compositions comprising at least one compound of the present invention, or an individual isomer, racemic or non-racemic mixture of isomers or a pharmaceutically acceptable salt or solvate thereof, together with at least one pharmaceutically acceptable carrier, and optionally other therapeutic and/or prophylactic ingredients.

In general, the compounds of the invention will be administered in a therapeutically effective amount by any of the accepted modes of administration for agents that serve similar utilities. Suitable dosage ranges are typically 1-500 mg daily, preferably 1-100 mg daily, and most preferably 1-30 mg daily, depending upon numerous factors such as the severity of the disease to be treated, the age and relative health of the subject, the potency of the compound used, the route and form of administration, the indication towards which the administration is directed, and the preferences and experience of the medical practitioner involved. One of ordinary skill in the art of treating such diseases will be able, without undue experimentation and in reliance upon personal knowledge and the disclosure of this Application, to ascertain a therapeutically effective amount of the compounds of the present invention for a given disease.

Compounds of the invention may be administered as pharmaceutical formulations including those suitable for oral (including buccal and sub-lingual), rectal, nasal, topical, pulmonary, vaginal, or parenteral (including intramuscular, intraarterial, intrathecal, subcutaneous and intravenous) administration or in a form suitable for administration by inhalation or insufflation. The preferred manner of administration is generally oral using a convenient daily dosage regimen which can be adjusted according to the degree of affliction.

A compound or compounds of the invention, together with one or more conventional adjuvants, carriers, or diluents, may be placed into the form of pharmaceutical compositions and unit dosages. The pharmaceutical compositions and unit dosage forms may be comprised of conventional ingredients in conventional proportions, with or without additional active compounds or principles, and the unit dosage forms may contain any suitable effective amount of the active ingredient commensurate with the intended daily dosage range to be employed. The pharmaceutical compositions may be employed as solids, such as tablets or filled capsules, semisolids, powders, sustained release formulations, or liquids such as solutions, suspensions, emulsions, elixirs, or filled capsules for oral use; or in the form of suppositories for rectal or vaginal administration; or in the form of sterile injectable solutions for parenteral use. Formulations containing about one (1) milligram of active ingredient or, more broadly, about 0.01 to about one hundred (100) milligrams, per tablet, are accordingly suitable representative unit dosage forms.

The compounds of the invention may be formulated in a wide variety of oral administration dosage forms. The pharmaceutical compositions and dosage forms may comprise a compound or compounds of the present invention or pharmaceutically acceptable salts thereof as the active component. The pharmaceutically acceptable carriers may be either solid or liquid. Solid form preparations include powders, tablets, pills, capsules, cachets, suppositories, and dispersible granules. A solid carrier may be one or more substances which may also act as diluents, flavouring agents, solubilizers, lubricants, suspending agents, binders, preservatives, tablet disintegrating agents, or an encapsulating material. In powders, the carrier generally is a finely divided solid which is a mixture with the finely divided active component. In tablets, the active component generally is mixed with the carrier having the necessary binding capacity in suitable proportions and compacted in the shape and size desired. The powders and tablets preferably contain from about one (1) to about seventy (70) percent of the active compound. Suitable carriers include but are not limited to magnesium carbonate, magnesium stearate, talc, sugar, lactose, pectin, dextrin, starch, gelatine, tragacanth, methylcellulose, sodium carboxymethylcellulose, a low melting wax, cocoa butter, and the like. The term "preparation" is intended to include the formulation of the active compound with encapsulating material as carrier, providing a capsule in which the active component, with or without carriers, is surrounded by a carrier, which is in association with it. Similarly, cachets and lozenges are included. Tablets, powders, capsules, pills, cachets, and lozenges may be as solid forms suitable for oral administration.

Other forms suitable for oral administration include liquid form preparations including emulsions, syrups, elixirs, aqueous solutions, aqueous suspensions, or solid form preparations which are intended to be converted shortly before use to liquid form preparations. Emulsions may be prepared in solutions, for example, in aqueous propylene glycol solutions or may contain emulsifying agents, for example, such as lecithin, sorbitan monooleate, or acacia. Aqueous solutions can be prepared by dissolving the active component in water and adding suitable colorants, flavors, stabilizers, and thickening agents. Aqueous suspensions can be prepared by dispersing the finely divided active component in water with viscous material, such as natural or synthetic gums, resins, methylcellulose, sodium carboxymethylcellulose, and other well known suspending agents. Solid form preparations include solutions, suspensions, and emulsions, and may contain, in addition to the active component, colorants, flavors, stabilizers, buffers, artificial and natural sweeteners, dispersants, thickeners, solubilizing agents, and the like.

The compounds of the invention may be formulated for parenteral administration (e.g., by injection, for example bolus injection or continuous infusion) and may be presented in unit dose form in ampoules, pre-filled syringes, small volume infusion or in multi-dose containers with an added preservative. The compositions may take such forms as suspensions, solutions, or emulsions in oily or aqueous vehicles, for example solutions in aqueous polyethylene glycol. Examples of oily or nonaqueous carriers, diluents, solvents or vehicles include propylene glycol, polyethylene glycol, vegetable oils (e.g., olive oil), and injectable organic esters (e.g., ethyl oleate), and may contain formulatory agents such as preserving, wetting, emulsifying or suspending, stabilizing and/or dispersing agents. Alternatively, the active ingredient may be in powder form, obtained by aseptic isolation of sterile solid or by lyophilization from solution for constitution before use with a suitable vehicle, e.g., sterile, pyrogen-free water.

The compounds of the invention may be formulated for topical administration to the epidermis as ointments, creams or lotions, or as a transdermal patch. Ointments and creams may, for example, be formulated with an aqueous or oily base with the addition of suitable thickening and/or gelling agents. Lotions may be formulated with an aqueous or oily base and will in general also containing one or more emulsifying agents, stabilizing agents, dispersing agents, suspending agents, thickening agents, or coloring agents. Formulations suitable for topical administration in the mouth include lozenges comprising active agents in a flavored base, usually sucrose and acacia or tragacanth; pastilles comprising the active ingredient in an inert base such as gelatine and glycerine or sucrose and acacia; and mouthwashes comprising the active ingredient in a suitable liquid carrier.

The compounds of the invention may be formulated for administration as suppositories. A low melting wax, such as a mixture of fatty acid glycerides or cocoa butter is first melted and the active component is dispersed homogeneously, for example, by stirring. The molten homogeneous mixture is then poured into convenient sized molds, allowed to cool, and to solidify.

The compounds of the invention may be formulated for vaginal administration. Pessaries, tampons, creams, gels, pastes, foams or sprays containing in addition to the active ingredient such carriers as are known in the art to be appropriate.

The subject compounds may be formulated for nasal administration. The solutions or suspensions are applied directly to the nasal cavity by conventional means, for example, with a dropper, pipette or spray. The formulations may be provided in a single or multidose form. In the latter case of a dropper or pipette, this may be achieved by the patient administering an appropriate, predetermined volume of the solution or suspension. In the case of a spray, this may be achieved for example by means of a metering atomizing spray pump.

The compounds of the invention may be formulated for aerosol administration, particularly to the respiratory tract and including intranasal administration. The compound will generally have a small particle size for example of the order of five (5) microns or less. Such a particle size may be obtained by means known in the art, for example by micronization. The active ingredient is provided in a pressurized pack with a suitable propellant such as a chlorofluorocarbon (CFC), for example, dichlorodifluoromethane, trichlorofluoromethane, or dichlorotetrafluoroethane, or carbon dioxide or other suitable gas. The aerosol may conveniently also contain a surfactant such as lecithin. The dose of drug may be controlled by a metered valve. Alternatively the active ingredients may be provided in a form of a dry powder, for example a powder mix of the compound in a suitable powder base such as lactose, starch, starch derivatives such as hydroxypropylmethyl cellulose and polyvinylpyrrolidine (PVP). The powder carrier will form a gel in the nasal cavity. The powder composition may be presented in unit dose form for example in capsules or cartridges of e.g., gelatine or blister packs from which the powder may be administered by means of an inhaler.

When desired, formulations can be prepared with enteric coatings adapted for sustained or controlled release administration of the active ingredient. For example, the compounds of the present invention can be formulated in transdermal or subcutaneous drug delivery devices. These delivery systems are advantageous when sustained release of the compound is necessary and when patient compliance with a treatment regimen is crucial. Compounds in transdermal delivery systems are frequently attached to an skin-adhesive solid support. The compound of interest can also be combined with a penetration enhancer, e.g., Azone (1-dodecylazacycloheptan-2-one). Sustained release delivery systems are inserted subcutaneously into the subdermal layer by surgery or injection. The subdermal implants encapsulate the compound in a lipid soluble membrane, e.g., silicone rubber, or a biodegradable polymer, e.g., polylactic acid.

The pharmaceutical preparations are preferably in unit dosage forms. In such form, the preparation is subdivided into unit doses containing appropriate quantities of the active component. The unit dosage form can be a packaged preparation, the package containing discrete quantities of preparation, such as packeted tablets, capsules, and powders in vials or ampoules. Also, the unit dosage form can be a capsule, tablet, cachet, or lozenge itself, or it can be the appropriate number of any of these in packaged form.

Other suitable pharmaceutical carriers and their formulations are described in *Remington: The Science and Practice of Pharmacy* 1995, edited by E. W. Martin, Mack Publishing Company, 19th edition, Easton, Pa. Representative pharmaceutical formulations containing a compound of the present invention are described below.

EXAMPLES

The following preparations and examples are given to enable those skilled in the art to more clearly understand and to practice the present invention. They should not be considered as limiting the scope of the invention, but merely as being illustrative and representative thereof.

Example 1

(7-Benzenesulfonyl-2,3-dihydro-benzo[1,4]dioxin-2-(R)-ylmethyl)-methyl-amine

The synthetic procedure of Example 1 is outlined in Scheme D below.

SCHEME D

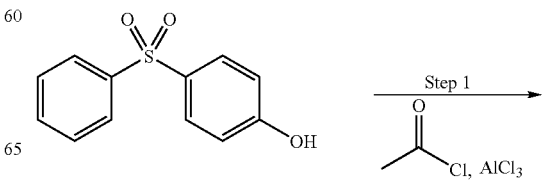

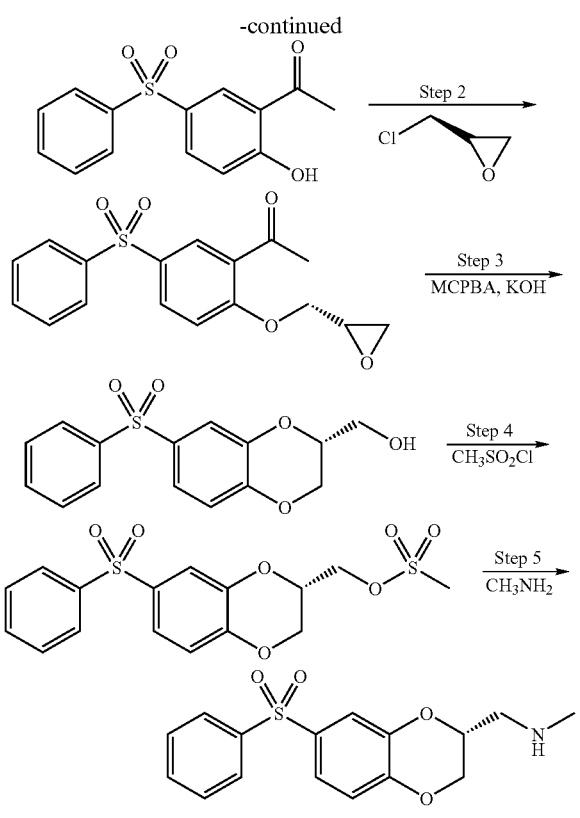

Step 1

1(5-Benzenesulfonyl-2-hydroxy-phenyl)-ethanone

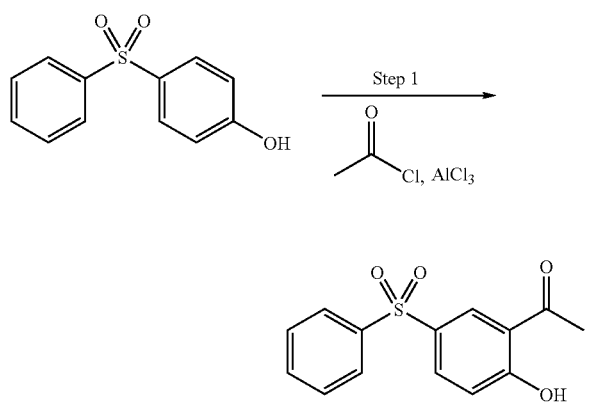

The 4-benzenesulfonyl-phenol used in step 1 was prepared according to the procedure described by Sung-Eun et al. in EP 0 514 935 B1, by treating anisole with benzensulfonyl chloride in the presence of AlCl₃, and treating the resulting compound with HBr in acetic acid under reflux to afford 4-benzenesulfonyl-phenol.

Chloroacetyl chloride (2.35 g; 0.030 mol) was added at 0° C. to a solution of 4-benzenesulfonyl-phenol (2.34 g; 0.010 mol) in carbon disulfide (50 mL). After 10 minutes at ambient temperature, aluminum trichloride was added in small portions. The reaction was heated at 130° C. under reflux, and the carbon disulfide was distilled, after which the reaction was heated at 180° C. for 45 minutes. After cooling to ambient temperature, the mixture was treated with 10% aqueous HCl (25 mL), extracted with ethyl acetate (100 mL×2), dried (Na₂SO₄) and concentrated in vacuo. The solid residue was purified by column chromatography on silica gel (hexane-ethyl acetate; 7:3) to give 1-(5-benzenesulfonyl-2-hydroxy-phenyl)-ethanone as a white solid (1.924 g; 70%). A sample was recrystallized from ethyl acetate-hexane: MS; (M)⁺ 276, m. p. 155.5-157.3° C.

Similarly, 1-[5-(3-Fluoro-benzenesulfonyl)-2-hydroxy-phenyl]-ethanone was prepared: M. p. 164.5-165.1° C.

Step 2

1-(5-Benzenesulfonyl-2-(S)-oxiranylmethoxy-phenyl)-ethanone

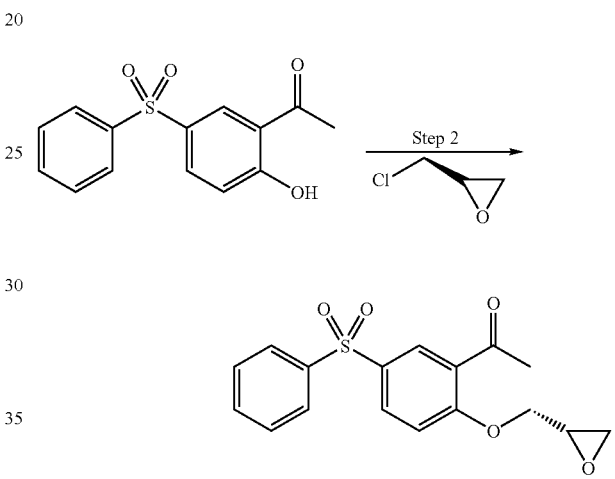

(R)-(−)Epichlorhydrin (1.93 g; 0.021 mol) was added to a suspension of 1-(5-benzenesulfonyl-2-hydroxy-phenyl)-ethanone (1.92 g; 0.007 mol) and potassium carbonate (1.44 g; 0.011 mol) in acetonitrile (5 mL). The mixture was heated under reflux for 18 hours. After cooling to ambient temperature, the mixture was diluted with ethyl acetate, filtered, washed with water and saturated sodium bicarbonate, dried (Na₂SO₄) and concentrated in vacuo. The crude material was purified by flash chromatography on silica gel (hexane-ethyl acetate; 7:3) to give 1-(5-benzene sulfonyl-2-(S)-oxiranylmethoxy-phenyl)-ethanone as a white solid (1.456 g; 63%). A sample was recrystallized from diethyl ether-hexane: M. p. 115.1-116.8° C. Similarly, but replacing (R)-(−)epichlorhydrin with (S)-(+)epichlorhydrin, 1-(5-benzene sulfonyl-2-(R)-oxiranylmethoxy-phenyl)-ethanone was prepared. M. p. 111.9-113.5° C. Similarly, but replacing 1-(5-benzenesulfonyl-2-hydroxy-phenyl)-ethanone with 1-[5-(3-fluoro-benzenesulfonyl)-2-hydroxy-phenyl]-ethanone, the above procedure gave 1-[5-(3-fluoro-benzenesulfonyl)-2-(S)-oxiranylmethoxy-phenyl]-ethanone: M. p. 112.7-114.9° C. Replacing 1-(5-benzenesulfonyl-2-hydroxy-phenyl)-ethanone with 1-[5-(3-Fluoro-benzenesulfonyl)-2-hydroxy-phenyl]-ethanone and replacing (R)-(−)epichlorhydrin with (S)-(+)epichlorhydrin gave 1-[5-(3-Fluoro-benzenesulfonyl)-2-(R)-oxiranylmethoxy-phenyl]-ethanone. M. p. 118.3-120.5° C.

Step 3

(7-Benzenesulfonyl-2,3-dihydro-benzo[1,4]dioxin-2-(R)-yl)-methanol

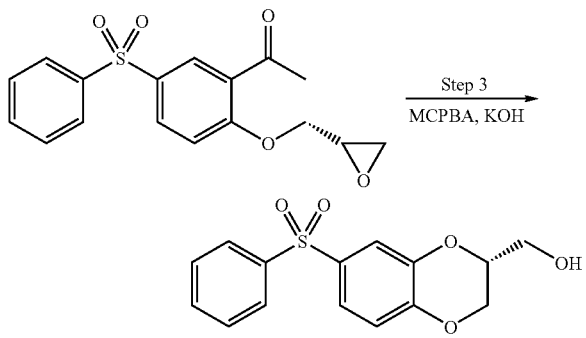

A solution of 1-(5-benzenesulfonyl-2-(S)-oxiranyl-methoxy-phenyl)-ethanone (2.04 g; 0.059 mol) and meta-chloroperoxybenzoic acid (4.13 g; 0.018 mol, max. 77%) in chloroform (20 mL) was heated under reflux for 18 hours. After cooling to ambient temperature the mixture was diluted with chloroform, filtered, washed with water and saturated sodium bicarbonate, dried ($Na_2SO_4$) and concentrated in vacuo. This crude residue (0.85 g; 0.0024 mol) dissolved in methanol (5 mL) was added to a solution of 10% aqueous potassium hydroxide (4 mL) at 0° C. The mixture was stirred for 30 minutes at room temperature. Solvent was removed in vacuo, and the residue was dissolve in ethyl acetate, washed with 10% aqueous hydrochloric acid followed by saturated brine, dried ($Na_2SO_4$) and concentrated in vacuo to give (7-benzenesulfonyl-2,3-dihydro-benzo[1,4]dioxin-2(R)-yl)-methanol as an oil (1.44 g; 77%): MS (M+H)$^+$ 307.

Step 4

Methanesulfonic acid 7-benzenesulfonyl-2,3-dihydro-benzo[1,4]dioxin-2-(S)-ylmethyl ester

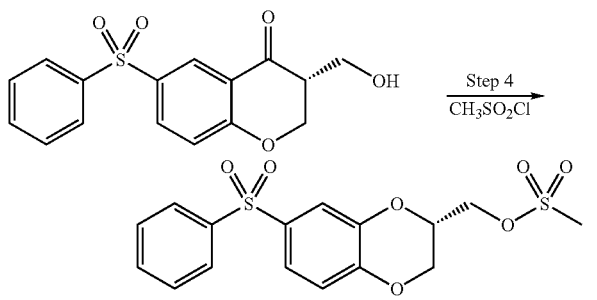

Methanesulfonyl chloride (0.550 g; 0.0048 mol) at 0° C. was added drop-wise to a solution of (7-benzenesulfonyl-2,3-dihydro-benzo[1,4]dioxin-2(R)-yl)-methanol (0.73 g; 0.00238 mol) and triethyl amine (0.48 g; 0.0048 mol) in dichloromethane (10 mL). The mixture was stirred at 0° C. for 45 minutes, and then diluted with dichloromethane (20 mL), washed with water, dried ($Na_2SO_4$) and concentrated in vacuo. The crude material was purified by flash chromatography on silica gel (hexane-ethyl acetate; 1:1) to give methansulfonic acid 7-benzenesulfonyl-2,3-dihydro-benzo[1,4]dioxin-2(S)-yl-methyl ester as a foam (0.67 g; 73%): MS (M+H)$^+$ 385.

Step 5

(7-Benzenesulfonyl-2,3-dihydro-benzo[1,4]dioxin-2-(R)-ylmethyl)-methyl-amine

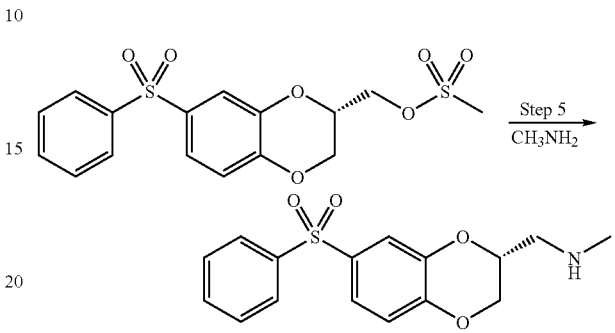

A 2M solution of methyl amine in methanol (10 mL) and methansulfonic acid 7-benzenesulfonyl-2,3-dihydro-benzo[1,4]dioxin-2(S)-yl-methyl ester (0.87 g, 2.26 mmol) were heated in a microwave at 100° C. for 3 hours. The solvent was removed under reduced pressure and the crude material was purified by flash chromatography on silica gel (eluting with dichloromethane—methanol; 98:2, v/v) to give (7-Benzenesulfonyl-2,3-dihydro-benzo[1,4]dioxin-2(R)-ylmethyl)-methyl-amine as a white solid (0.557 g; 77%), which was converted to a hydrochloride salt: MS (M)$^+$ 319; m. p. 240.0-243.6° C., [α]=+40.5° (methanol; c=1).

Similarly prepared were:

(7-Benzenesulfonyl-2,3-dihydro-benzo[1,4]dioxin-2(S)-ylmethyl)-methyl-amine hydrochloride salt: MS (M)$^+$ 319; m. p. 247.1-249.9° C., [α]=−40° (methanol; c=1);

[7-(3-Fluoro-benzenesulfonyl)-2,3-dihydro-benzo[1,4]dioxin-2(R)-ylmethyl]-methyl-amine hydrochloride salt: MS (M+H)$^+$ 338; m. p. 245.8-246.4° C., [α]=+40° (methanol; c=0.5); and

[7-(3-Fluoro-benzenesulfonyl)-2,3-dihydro-benzo[1,4]dioxin-2(S)-ylmethyl]-methyl-amine hydrochloride salt: MS (M+H)$^+$ 338; m. p. 249.0-250.9° C., [α]=−40° (methanol; c=0.5).

Example 2

(7-Benzenesulfonyl-2,3-dihydro-benzo[1,4]dioxin-2-(R)-ylmethyl)-methyl-amine

Example 2 provides an alternate procedure for preparation of (7-benzenesulfonyl-2,3-dihydro-benzo[1,4]dioxin-2-(R)-ylmethyl)-methyl-amine, and is outlined in Scheme E below.

SCHEME E

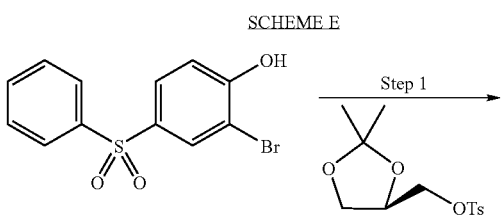

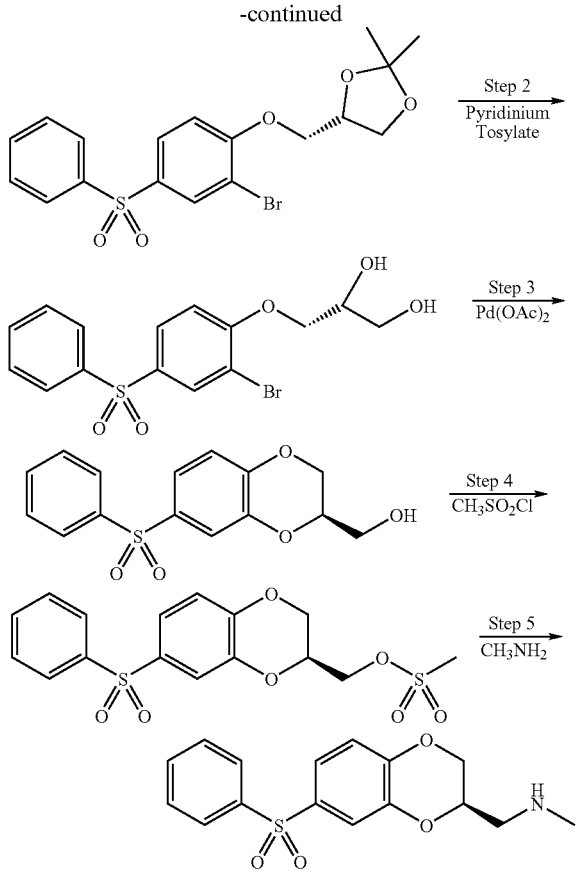

Step 1

4-(S)-(4-Benzenesulfonyl-2-bromo-phenoxymethyl)-2,2-dimethy-[3,3]dioxolan

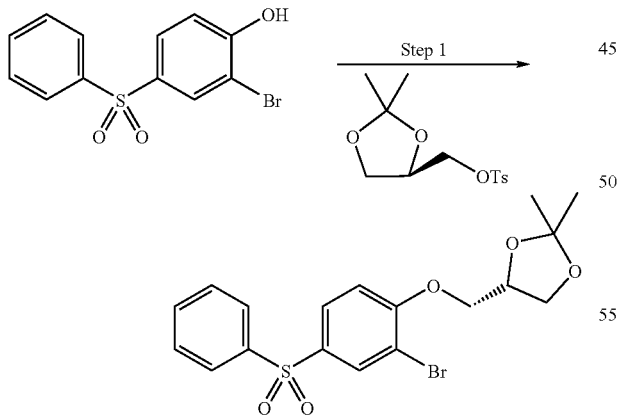

Toluene-4-(R)-sulfonic acid 2,2-dimethyl-[1,3]dioxolan-4-yl-methyl ester (0.99 g; 0.003 mol) was added to a suspension of 4-benzenesulfonyl-2-bromo-phenol (0.91 g; 0.003 mol, prepared by the procedure of Sung-Eun et al. as described in Example 1) and potassium carbonate (0.88 g; 0.0006 mol) in acetonitrile (4 mL). The mixture was heated under reflux for 72 hours. After cooling to ambient temperature the mixture was diluted with ethyl acetate, filtered, washed with water and saturated sodium bicarbonate, dried ($Na_2SO_4$) and concentrated in vacuo. The crude material was purified by crystallization from diethyl ether-hexane to give 4-(S)-(4-benzenesulfonyl-2-bromo-phenoxymethyl)-2, 2-dimethy-[3,3]dioxolan as a white crystalline (1.41 g; 84%). Mp. 115.8-118.5° C., [α]=+20.2° (methanol; c=1).

Step 2

3-(4-Benzenesulfonyl-2-bromo-phenoxy)-propane 1-2-(R)-diol

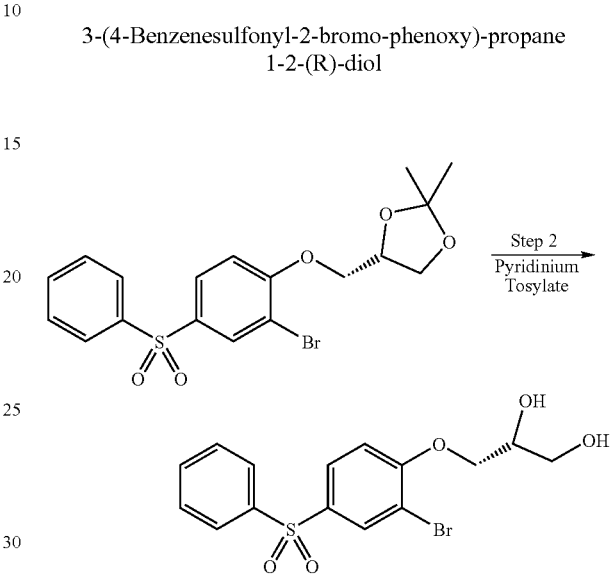

A solution of 4-(S)-(4-benzenesulfonyl-2-bromo-phenoxymethyl)-2,2-dimethyl-[3,3]dioxolan (1.07 g, 0.0025 mol) and pyridinum toluene-4-sulfonate (0.38 g, 0.0015 mol) in acetone (20 mL) and water (5 mL) was heated under reflux for 12 hours. The solvent was removed under reduced pressure. The oily residue was dissolved in ethyl acetate (100 mL), washed with cold 10% aqueous hydrochloric acid, saturated sodium bicarbonate, dried ($Na_2SO_4$) and concentrated in vacuo. Recrystallization of the residue (diethyl ether-hexane) gave 3-(4-benzenesulfonyl-2-bromo-phenoxy)-propane 1-2-(R)-diol as white crystals. Mp. 104.6-105.9° C.

Step 3

(7-Benzenesulfonyl-2,3-dihydro-benzo[1,4]dioxin-2-(R)-yl)-methanol

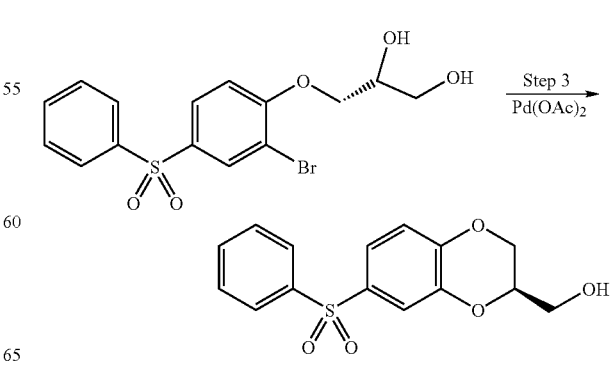

A suspension of 3-(4-benzenesulfonyl-2-bromo-phenoxy)-propane 1-2-(R)-diol (0.390 g, 0.001 mol), Pd(OAc)$_2$ (0.007 g, 0.00003 mol, 3 mol %), racemic-2-(di-t-butylphosphino)-1,1'-binaphthyl (0.012 g, 0.00003, 3 mol %) and K$_3$PO$_4$ (0.320 g, 0.0015, 1.5 equiv) in toluene (1 mL) was heated under argon atmosphere at 80° C. for 5 hours. After cooling to ambient temperature the mixture was diluted with ethyl acetate (1 mL), washed with water and saturated sodium chloride, dried (Na$_2$SO$_4$) and concentrated in vacuo. The crude material was purified by flash chromatography on silica gel (eluting with hexane-ethyl acetate; 1:1, v/v) to give (7-benzenesulfonyl-2,3-dihydro-benzo[1,4]dioxin-2(R)-yl)-methanol as an oil which solidified upon standing. (0.160 g; 52%). m. p. 112.0-113.5° C., [α]=+36.7° (CHCl$_3$, c=1).

Step 4

Methanesulfonic acid 7-benzenesulfonyl-2,3-dihydro-benzo[1,4]dioxin-2-(S)-ylmethyl ester

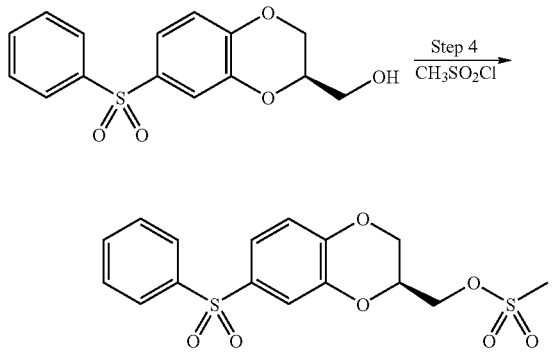

Using the procedure of step 4 of example 1, methanesulfonic acid 7-benzenesulfonyl-2,3-dihydro-benzo[1,4]dioxin-2-(S)-ylmethyl ester was prepared: MS ;+H)$^+$ 385.

Step 5

(7-Benzenesulfonyl-2,3-dihydro-benzo[1,4]dioxin-2-(R)-ylmethyl)-methyl-amine

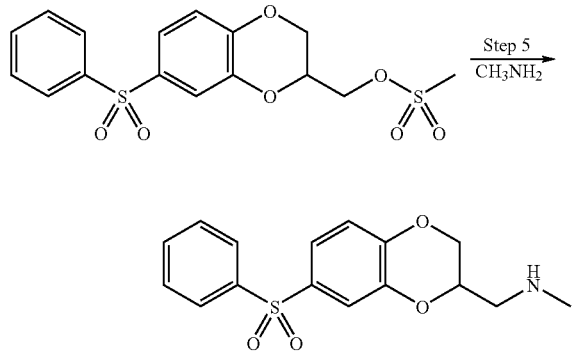

Using the procedure of step 5 of example 1, (7-benzenesulfonyl-2,3-dihydro-benzo[1,4]dioxin-2-(R)-ylmethyl)-methyl amine was prepared as a hydrochloride salt: MS; (M+H)$^+$ 320, m. p. 218.2-220.5° C., [α]=+49° (methanol; c=1).

Example 3

(6-Benzenesulfonyl-2,3-dihydro-benzo[1,4]dioxin-2-(S)-ylmethyl)-methyl-amine

The synthetic procedure of Example 3 is outlined in Scheme F below.

SCHEME F

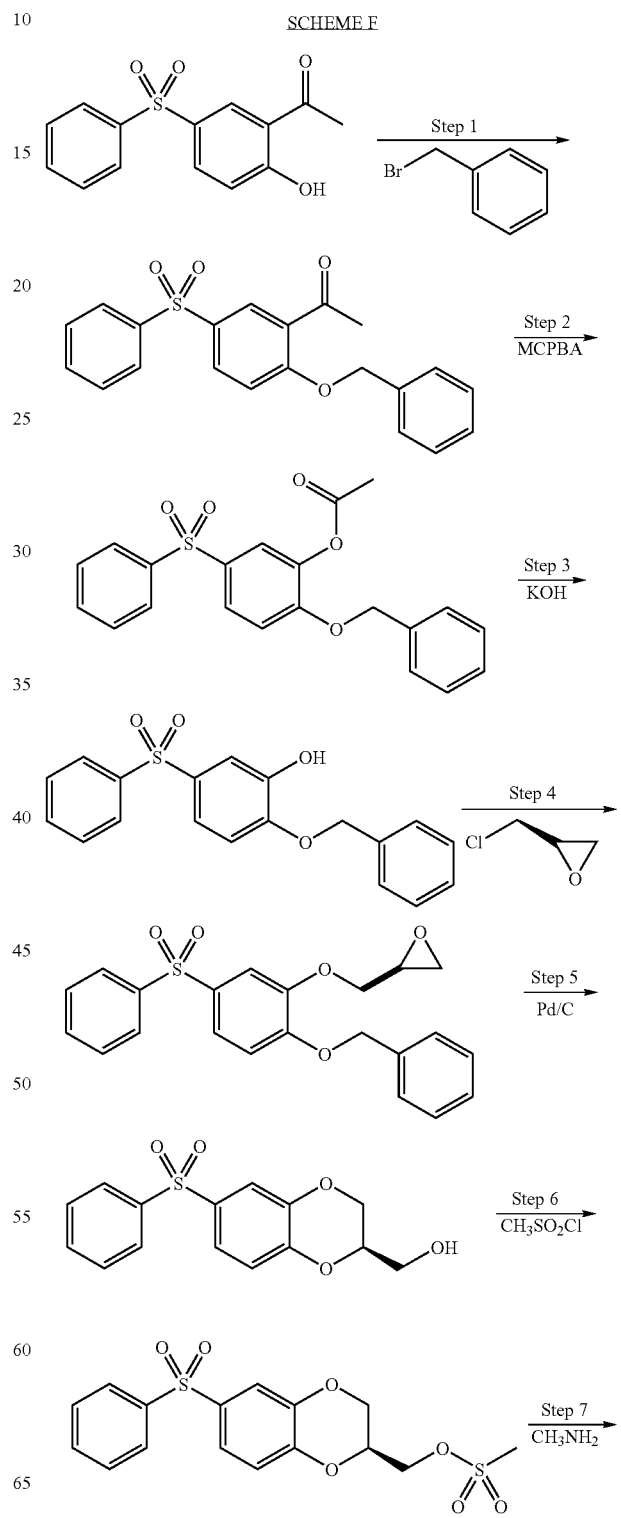

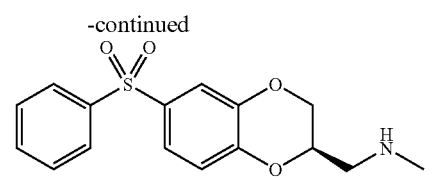

Step 1

1-(5-Benzenesulfonyl-2-benzyloxy-phenyl)-ethanone

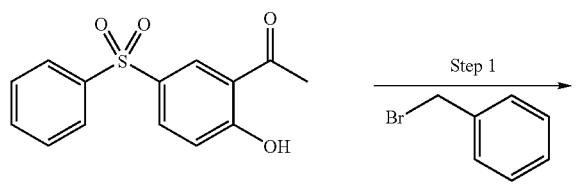

Benzyl bromide (1.443 g; 0.0087 mol) was added to a suspension of 1-(5-benzenesulfonyl-2-hydroxy-phenyl)-ethanone (2.01 g; 0.0073 mol) and potassium carbonate (2.01 g; 0.015 mol) in acetonitrile (5.0 mL). The mixture was heated under reflux for 18 hours. After cooling to ambient temperature, the mixture was diluted with ethyl acetate, filtered, washed with water and saturated sodium bicarbonate, dried (Na$_2$SO$_4$) and concentrated in vacuo. The crude material was purified by flash chromatography on silica gel (hexane-ethyl acetate; 7:3) to give 1-(5-benzenesulfonyl-2-benzyloxy-phenyl)-ethanone as a white solid (2.17 g; 81%). A sample was recrystallized from diethyl ether-hexane: M. p. 80.5-82.4° C.

Step 2

Acetic acid 5-benzenesulfonyl-2-benzyloxy-phenyl ester

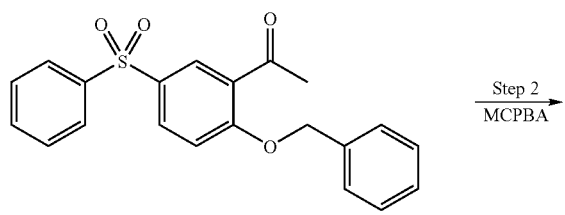

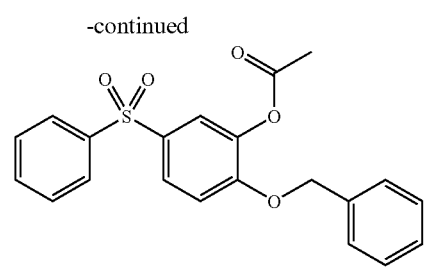

A solution of 1-(5-benzenesulfonyl-2-benzyloxy-phenyl)-ethanone (2.16 g; 0.059 mol) and meta-chloroperoxybenzoic acid (3.98 g; 0.018 mol, max. 77%) in chloroform (20 mL) was heated under reflux for 18 hours. After cooling to ambient temperature the mixture was diluted with chloroform, filtered, washed with water and saturated sodium bicarbonate, dried (Na$_2$SO$_4$) and concentrated in vacuo. The crude material was purified by flash chromatography on silica gel (hexane-ethyl acetate; 1:1) to give acetic acid 5-benzenesulfonyl-2-benzyloxy-phenyl ester (2.1 g; 93%): M. p. 106.9-111.1° C.

Step 3

5-Benzenesulfonyl-2-benzyloxy-phenol

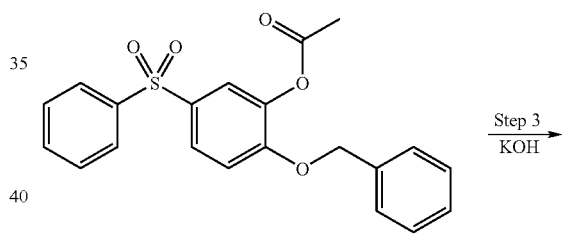

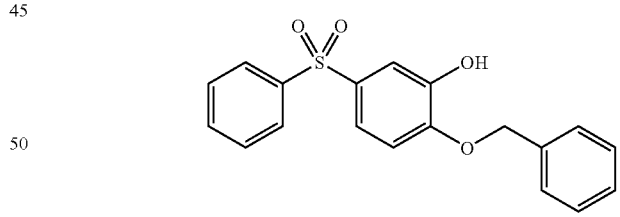

A solution of 10% aqueous potassium hydroxide (4 mL) at 0° C. was added to a solution of 5-benzenesulfonyl-2-benzyloxy-phenyl ester (1.18 g; 0.0031 mol) in methanol (5 mL), and the mixture was stirred for 30 minutes at room temperature. Solvent was removed in vacuo, and the residue was dissolve in ethyl acetate, washed with 10% aqueous hydrochloric acid, washed with brine, dried (Na$_2$SO$_4$) and concentrated in vacuo to give 5-benzenesulfonyl-2-benzyloxy-phenol as a white solid (0.865 g; 82.4%). A sample was recrystallized from diethyl ether: MS; (M−H)$^-$ 339; m. p. 144.5-147.8° C.

Step 4

2-(S)-(5-Benzenesulfonyl-2-benzyloxymethyl)-oxirane

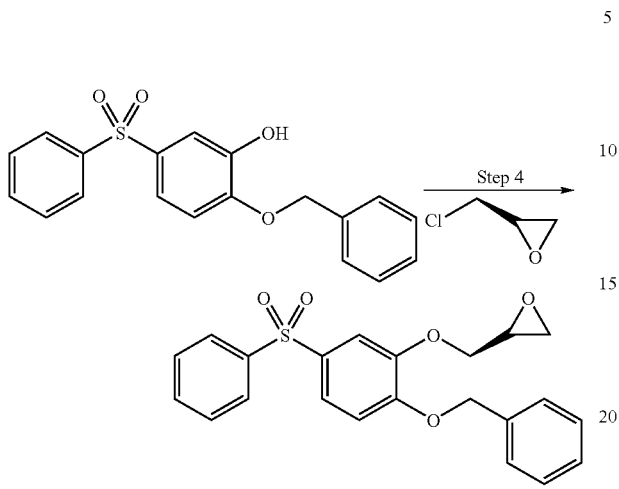

Follow the procedure of step 2 of Example 1 above, 2-(S)-(5-benzenesulfonyl-2-benzyloxymethyl)-oxirane was prepared: MS (M+H)+ 397. Similarly, 2-(R)-(5-benzenesulfonyl-2-benzyloxymethyl)-oxirane was prepared:

MS (M+H)+ 397.

Step 5

(6-Benzenesulfonyl-2,3-dihydro-benzo[1,4]dioxin-(R)-2-yl)-methanol

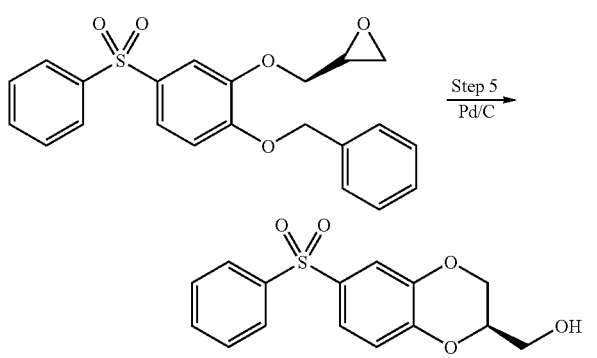

A mixture of 2-(S)-(5-benzenesulfonyl-2-benzyloxymethyl)-oxirane (0.29 g; 0.73 mmol), potassium formate (0.307 g; 0.0036 mol) and 10% palladium on charcoal (0.002 g) in ethanol (5 mL) was heated under reflux for 30 min. After cooling to ambient temperature the mixture was diluted with ethyl acetate and filtered through celite. The filtrate was washed with water, saturated sodium chloride, dried ($Na_2SO_4$) and concentrated in vacuo. The crude material was purified by flash chromatography on silica gel (eluting with hexane-ethyl acetate; 1:1, v/v) to give (6-benzenesulfonyl-2,3-dihydro-benzo[1,4]dioxin-2-(R)-yl)-methanol as an oil which solidified upon standing. (0.155 g; 69%); MS (M+H)+ 307.

Similarly, (6-benzenesulfonyl-2,3-dihydro-benzo[1,4]dioxin-2-(S)-yl)-methanol was prepared.

Step 6

Methanesulfonic acid 6-benzenesulfonyl-2,3-dihydro-benzo[1,4]dioxin-2-(S)-ylmethyl ester

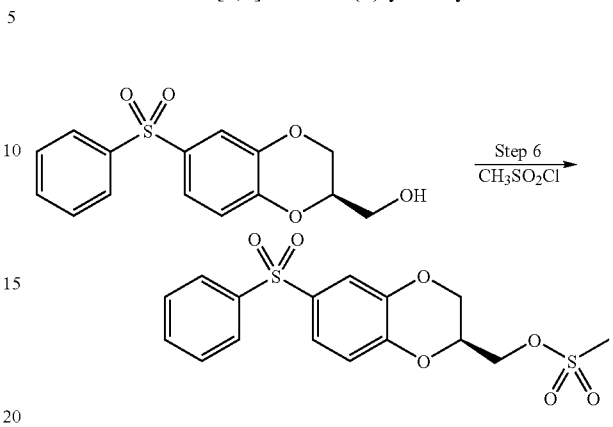

Using the procedure of step 4 of example 1, methanesulfonic acid 6-benzenesulfonyl-2,3-dihydro-benzo[1,4]dioxin-2-(S)-ylmethyl ester was prepared: MS (M+H)+ 385.

Similarly, methanesulfonic acid 6-benzenesulfonyl-2,3-dihydro-benzo[1,4]dioxin-2-(R)-ylmethyl ester was prepared.

Step 7

(6-Benzenesulfonyl-2,3-dihydro-benzo[1,4]dioxin-2-(R)-ylmethyl)-methyl amine

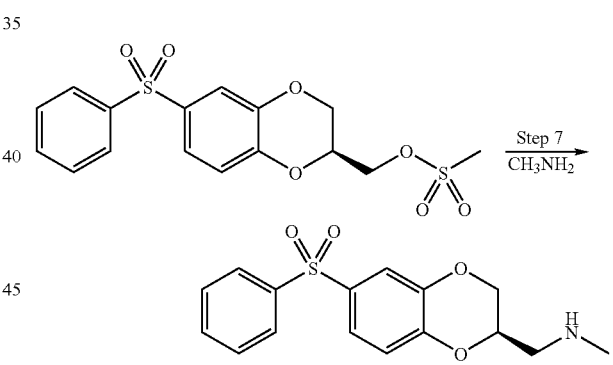

Using the procedure of step 5 of example 1, (6-benzenesulfonyl-2,3-dihydro-benzo[1,4]dioxin-2-(R)-ylmethyl)-methyl amine was prepared as a hydrochloride salt: MS; (M+H)+ 320, m. p. 218.2-220.5° C., [α]=+45° (methanol; c=1).

Following the same procedure, (6-benzenesulfonyl-2,3-dihydro-benzo[1,4]dioxin-2-(S)-yl-methyl)-methyl amine hydrochloride salt was also prepared: MS; (M+H)+ 320, m. p. 209.0-212.0° C., [α]=−44° (methanol; c=0.5).

Example 4

Formulations

Pharmaceutical preparations for delivery by various routes are formulated as shown in the following Tables. "Active ingredient" or "Active compound" as used in the Tables means one or more of the Compounds of Formula I.

| Composition for Oral Administration | |
| --- | --- |
| Ingredient | % wt./wt. |
| Active ingredient | 20.0% |
| Lactose | 79.5% |
| Magnesium stearate | 0.5% |

The ingredients are mixed and dispensed into capsules containing about 100 mg each; one capsule would approximate a total daily dosage.

| Composition for Oral Administration | |
| --- | --- |
| Ingredient | % wt./wt. |
| Active ingredient | 20.0% |
| Magnesium stearate | 0.5% |
| Crosscarmellose sodium | 2.0% |
| Lactose | 76.5% |
| PVP (polyvinylpyrrolidine) | 1.0% |

The ingredients are combined and granulated using a solvent such as methanol. The formulation is then dried and formed into tablets (containing about 20 mg of active compound) with an appropriate tablet machine.

| Composition for Oral Administration | |
| --- | --- |
| Ingredient | Amount |
| Active compound | 1.0 g |
| Fumaric acid | 0.5 g |
| Sodium chloride | 2.0 g |
| Methyl paraben | 0.15 g |
| Propyl paraben | 0.05 g |
| Granulated sugar | 25.5 g |
| Sorbitol (70% solution) | 12.85 g |
| Veegum K (Vanderbilt Co.) | 1.0 g |
| Flavoring | 0.035 ml |
| Colorings | 0.5 mg |
| Distilled water | q.s. to 100 ml |

The ingredients are mixed to form a suspension for oral administration.

| Parenteral Formulation | |
| --- | --- |
| Ingredient | % wt./wt. |
| Active ingredient | 0.25 g |
| Sodium Chloride | qs to make isotonic |
| Water for injection | 100 ml |

The active ingredient is dissolved in a portion of the water for injection. A sufficient quantity of sodium chloride is then added with stirring to make the solution isotonic. The solution is made up to weight with the remainder of the water for injection, filtered through a 0.2 micron membrane filter and packaged under sterile conditions.

| Suppository Formulation | |
| --- | --- |
| Ingredient | % wt./wt. |
| Active ingredient | 1.0% |
| Polyethylene glycol 1000 | 74.5% |
| Polyethylene glycol 4000 | 24.5% |

The ingredients are melted together and mixed on a steam bath, and poured into molds containing 2.5 g total weight.

| Topical Formulation | |
| --- | --- |
| Ingredients | grams |
| Active compound | 0.2-2 |
| Span 60 | 2 |
| Tween 60 | 2 |
| Mineral oil | 5 |
| Petrolatum | 10 |
| Methyl paraben | 0.15 |
| Propyl paraben | 0.05 |
| BHA (butylated hydroxy anisole) | 0.01 |
| Water | q.s. 100 |

All of the ingredients, except water, are combined and heated to about 60° C. with stirring. A sufficient quantity of water at about 60° C. is then added with vigorous stirring to emulsify the ingredients, and water then added q.s. about 100 g.

Nasal Spray Formulations

Several aqueous suspensions containing from about 0.025-0.5 percent active compound are prepared as nasal spray formulations. The formulations optionally contain inactive ingredients such as, for example, microcrystalline cellulose, sodium carboxymethylcellulose, dextrose, and the like. Hydrochloric acid may be added to adjust pH. The nasal spray formulations may be delivered via a nasal spray metered pump typically delivering about 50-100 microliters of formulation per actuation. A typical dosing schedule is 2-4 sprays every 4-12 hours.

Example 5

Radioligand Binding Studies

This example illustrates in vitro radioligand binding studies of compound of formula I.

The binding activity of compounds of this invention in vitro was determined as follows. Duplicate determinations of 5-$HT_6$ ligand affinity were made by competing for binding of [$^3$H]LSD in cell membranes derived from HEK293 cells stably expressing recombinant human 5-$HT_6$ receptor. Duplicate determinations of 5-$HT_{2A}$ ligand affinity were made by competing for binding of [$^3$H]Ketanserin (3-(2-(4-(4-fluorobenzoyl)piperidinol)ethyl)-2,4(1H,3H)-quinazolinedione) in cell membranes derived from CHO—K1 cells stably expressing recombinant human 5-$HT_{2A}$ receptor. Membranes were prepared from HEK 293 cell lines by the method described by Monsma et al., Molecular Pharmacology, Vol. 43 pp. 320-327 (1993), and from CHO—K1 cell lines as described by Bonhaus et al., Br J Pharmacol. June;1 15(4):622-8 (1995).

For estimation of affinity at the 5-HT$_6$ receptor, all determinations were made in assay buffer containing 50 mM Tris-HCl, 10 mM MgSO$_4$, 0.5 mM EDTA, 1 mM ascorbic acid, pH 7.4 at 37° C., in a 250 microliter reaction volume. For estimation of affinity at the 5-HT$_{2A}$ receptor all determinations were made in assay buffer containing 50 mM Tris-HCl, 5 mM ascorbic acid, 4 mM CaCl2, pH 7.4 at 32° C., in a 250 microliter reaction volume.

Assay tubes containing [$^3$H] LSD or [$^3$H]Ketanserin (5 nM), competing ligand, and membrane were incubated in a shaking water bath for 75 min. at 37° C. (for 5-HT$_6$) or 60 min. at 32° C. (for 5-HT$_{2A}$), filtered onto Packard GF-B plates (pre-soaked with 0.3% PEI) using a Packard 96 well cell harvester and washed 3 times in ice cold 50 mM Tris-HCl. Bound [$^3$H] LSD or [$^3$H]Ketanserin were determined as radioactive counts per minute using Packard TopCount.

Displacement of [$^3$H]LSD or [$^3$H]Ketanserin from the binding sites was quantified by fitting concentration-binding data to a 4-parameter logistic equation:

$$\text{binding} = \text{basal} + \left( \frac{B\text{max} - \text{basal}}{1 + 10^{-Hill(\log[ligand] - \log IC_{50})}} \right)$$

where Hill is the Hill slope, [ligand] is the concentration of competing radioligand and IC$_{50}$ is the concentration of radioligand producing half-maximal specific binding of radioligand. The specific binding window is the difference between the Bmax and the basal parameters. Using the procedures of this Example, compounds of Formula I were tested and found to be selective 5-HT$_6$ antagonists, selective 5-HT$_{2A}$ antagonists, or both. For example, the compound (7-Benzenesulfonyl-2,3-dihydro-benzo[1,4]dioxin-2-(R)-ylmethyl)-methyl-amine exhibted a pKi of approximately 9.78 for the 5-HT6 receptor, and [7-(3-Fluoro-benzenesulfonyl)-2,3-dihydro-benzo[1,4]dioxin-2-(S)-ylmethyl]-methyl-amine exhibted a pKi of approximately 7.74 for the 5-HT2A receptor.

Example 6

Cognition Enhancement

The cognition-enhancing properties of compounds of the invention may be in a model of animal cognition: the object recognition task model. 4-month-old male Wistar rats (Charles River, The Netherlands) were used. Compounds were prepared daily and dissolved in physiological saline and tested at three doses. Administration was always given i.p. (injection volume 1 ml/kg) 60 minutes before T1. Scopolamine hydrobromide was injected 30 minutes after compound injection. Two equal testing groups were made of 24 rats and were tested by two experimenters. The testing order of doses was determined randomly. The experiments were performed using a double blind protocol. All rats were treated once with each dose condition. The object recognition test was performed as described by Ennaceur, A., Delacour, J., 1988, A new one-trial test for neurobiological studies of memory in rats. 1: Behavioral data. *Behav. Brain Res.* 31, 47-59.

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective, spirit and scope of the present invention. All such modifications are intended to be within the scope of the claims appended hereto.

What is claimed is:
1. A compound of formula I:

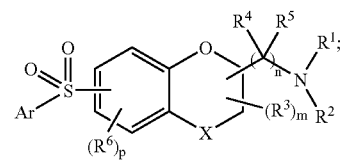

or a pharmaceutically acceptable salt thereof,
wherein:
m is from 0 to 3;
n is from 1 to 3;
p is from 0 to 3;
Ar is optionally substituted aryl;
X is —O—;
R$^1$ and R$^2$ each independently is hydrogen, C$_{1-6}$alkyl, or C$_{1-6}$alkoxy-C$_{1-6}$alkyl, or hydroxy-C$_{1-6}$ alkyl;
or one of R$^1$ and R$^2$ is hydrogen or C$_{1-6}$alkyl and the other is C$_{1-6}$alkylcarbonyl, C$_{3-8}$cycloalkyl, aryl-C$_{1-6}$alkyl, hydroxy, or a five- or six-membered heteroaryl or heterocyclyl that contains one or two nitrogens;
or R$^1$ and R$^2$ together with the nitrogen to which they are attached may form a three- to seven-membered ring that optionally contains an additional heteroatom selected from N, O and S;
or R$^1$ and R$^2$ together with the nitrogen to which they are attached may form a guanidinyl group of the formula

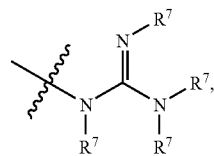

a carbamyl group of the formula

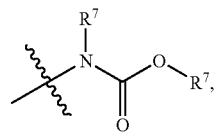

or a urea group of the formula

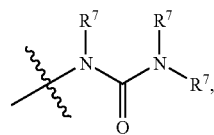

wherein each R$^7$ is independently hydrogen or C$_{1-6}$alkyl;

each $R^3$ is independently $C_{1-6}$alkyl, hydroxy-$C_{1-6}$alkyl or $C_{1-6}$alkoxy-$C_{1-6}$alkyl;

or two of $R^3$ together with the atoms to which they are attached may form a $C_{4-6}$carbocyclic ring;

$R^4$ and $R^5$ each independently is hydrogen or $C_{1-6}$ alkyl; and each $R^6$ is independently halo, $C_{1-6}$alkyl, halo-$C_{1-6}$alkyl, or —$SR^c$, where $R^c$ is hydrogen or $C_{1-6}$alkyl.

2. The compound of claim 1, wherein $R^4$ and $R^5$ are hydrogen.

3. The compound of claim 1, wherein m is 0.

4. The compound of claim 1, wherein n is 1 or 2.

5. The compound of claim 1, wherein $R^1$ and $R^2$ each independently is hydrogen or $C_{1-6}$alkyl, or $R^1$ and $R^2$ together with the nitrogen to which they are attached form a three, four, five or six-membered ring.

6. The compound of claim 2, wherein $R^4$ and $R^5$ are hydrogen.

7. The compound of claim 6, wherein n is 1.

8. The compound of claim 7, wherein m is 0.

9. The compound of claim 1, wherein p is 0.

10. The compound of claim 9, wherein $R^1$ and $R^2$ each independently is hydrogen or $C_{1-6}$alkyl.

11. The compound of claim 10, wherein Ar is optionally substituted phenyl.

12. The compound of claim 1, wherein said compound is of the formula III:

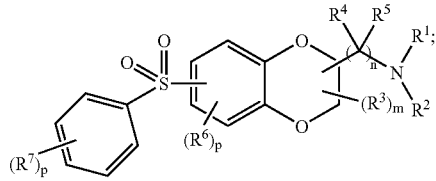

wherein:

n is 1 or 2;

q is from 0 to 4;

each $R^7$ is independently halo, $C_{1-6}$alkyl, halo-$C_{1-6}$alkyl, hetero-$C_{1-6}$alkyl, cyano, —$SO_2R^b$, —C(=O)—$NR^cR^d$, —$SR^c$, —C(=O)—$R^c$, where each of $R^b$, $R^c$ and $R^d$ is independently hydrogen or $C_{1-6}$alkyl; and m, p, $R^1$, $R^2$, $R^3$, $R^4$, $R^5$ and $R^6$ are as recited in claim 1.

13. The compound of claim 12, wherein q is 0.

14. The compound of claim 12, wherein q is 1 and $R^7$ is halo.

15. The compound of claim 12, wherein said compound is of the formula IV:

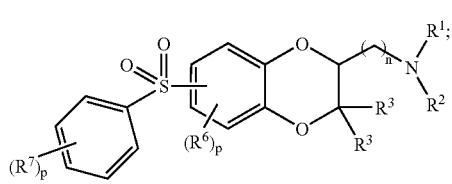

wherein n, p, q, $R^1$, $R^2$, $R^3$, $R^6$ and $R^7$ are as recited in claim 12.

16. The compound of claim 12, wherein said compound is of the formula V:

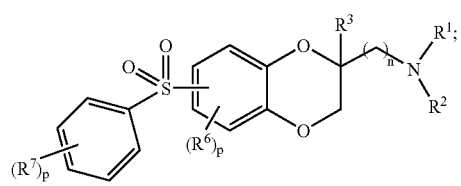

wherein n, p, q, $R^1$, $R^2$, $R^3$, $R^6$ and $R^7$ are as recited in claim 12.

17. The compound of claim 12, wherein said compound is of the formula VI:

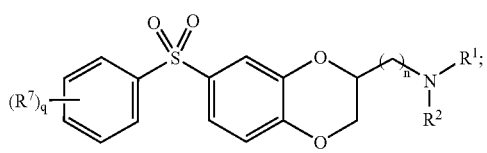

wherein n, q, $R^1$, $R^2$ and $R^7$ are as recited in claim 12.

18. The compound of claim 12, wherein said compound is of the formula VII:

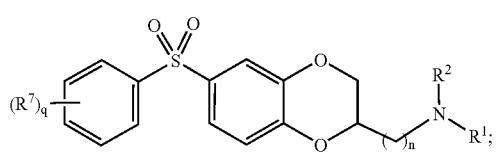

wherein n, q, $R^1$, $R^2$ and $R^7$ are as recited in claim 12.

19. The compound of claim 17, wherein said compound is of formula VIII:

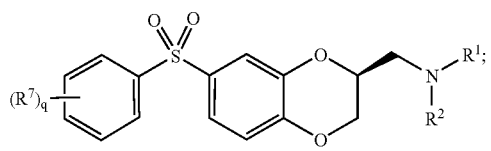

wherein q, R1, R2, and R7 are as recited in claim 17.

20. The compound of claim 17, wherein said compound is of formula IX:

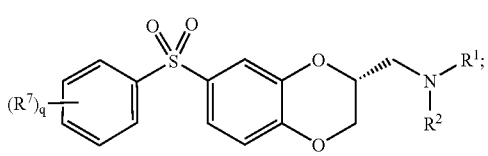

wherein q, $R^1$, $R^2$ and $R^7$ are as recited in claim 17.

21. The compound of claim 19, wherein:

q is 0 or 1;

$R^7$ is halo; and one of $R^1$ and $R^2$ is $C_{1-6}$alkyl and the other is hydrogen.

22. A compound selected from the group consisting of:
(+−)-(7-Benzenesulfonyl-2,3-dihydro-benzo[1,4]dioxin-2-ylmethyl)-methyl-amine;
(7-Benzenesulfonyl-2,3-dihydro-benzo[1,4]dioxin-2-(S)-ylmethyl)-methyl-amine;
(7-Benzenesulfonyl-2,3-dihydro-benzo[1,4]dioxin-2-(R)-ylmethyl)-methyl-amine;
(6-Benzenesulfonyl-2,3-dihydro-benzo[1,4]dioxin-2-(R)-ylmethyl)-methyl-amine;
(6-Benzenesulfonyl-2,3-dihydro-benzo[1,4]dioxin-2-(S)-ylmethyl)-methyl-amine;
(7-Benzenesulfonyl-2,3-dihydro-benzo[1,4]dioxin-2-yl)-methylamine;
[7-(3-Fluoro-benzenesulfonyl)-2,3-dihydro-benzo[1,4]dioxin-2-(S)-ylmethyl]-methyl-amine;
[7-(3-Fluoro-benzenesulfonyl)-2,3-dihydro-benzo[1,4]dioxin-2-(R)-ylmethyl]-methyl-amine;
C-[7-(3-Fluoro-benzenesulfonyl)-2,3-dihydro-benzo[1,4]dioxin-2-(S)-yl]-methylamine;
1-(7-Benzenesulfonyl-2,3-dihydro-benzo[1,4]dioxin-2-(R)-ylmethyl)-pyrrolidine;
Benzyl-[7-(3-fluoro-benzenesulfonyl)-2,3-dihydro-benzo[1,4]dioxin-2-ylmethyl]-amine;
Methyl-[7-(toluene-4-sulfonyl)-2,3-dihydro-benzo[1,4]dioxin-2-ylmethyl]-amine;
Ethyl-[7-(3-fluoro-benzenesulfonyl)-2,3-dihydro-benzo[1,4]dioxin-2-ylmethyl]-amine;
[7-(3-Fluoro-benzenesulfonyl)-2,3-dihydro-benzo[1,4]dioxin-2-ylmethyl]-dimethyl-amine;
[7-(3-Fluoro-benzenesulfonyl)-2,3-dihydro-benzo[1,4]dioxin-2-ylmethyl]-isopropyl-amine;
1-[7-(3-Fluoro-benzenesulfonyl)-2,3-dihydro-benzo[1,4]dioxin-2-ylmethyl]-azetidine;
[7-(3-Fluoro-benzenesulfonyl)-2,3-dihydro-benzo[1,4]dioxin-2-ylmethyl]-(2-methoxy-ethyl)-amine;
4-[7-(3-Fluoro-benzenesulfonyl)-2,3-dihydro-benzo[1,4]dioxin-2-ylmethyl]-morpholine;
1-(7-Benzenesulfonyl-2,3-dihydro-benzo[1,4]dioxin-2-ylmethyl)-azetidine;
1-[7-(3-Fluoro-benzenesulfonyl)-2,3-dihydro-benzo[1,4]dioxin-2-ylmethyl]-aziridine;
(7-Benzenesulfonyl-2,3-dihydro-benzo[1,4]dioxin-2-ylmethyl)-benzyl-amine;
C-(7-Benzenesulfonyl-2,3-dihydro-benzo[1,4]dioxin-2-yl)-methylamine;
(7-Benzenesulfonyl-2,3-dihydro-benzo[1,4]dioxin-2-ylmethyl)-dimethyl-amine;
(7-Benzenesulfonyl-2,3-dihydro-benzo[1,4]dioxin-2-ylmethyl)-isopropyl-amine;
1-(7-Benzenesulfonyl-2,3-dihydro-benzo[1,4]dioxin-2-ylmethyl)-aziridine;
(7-Benzenesulfonyl-2,3-dihydro-benzo[1,4]dioxin-2-ylmethyl)-(2-methoxy-ethyl)-amine;
(7-Benzenesulfonyl-2,3-dihydro-benzo[1,4]dioxin-2-ylmethyl)-ethyl-amine;
Methyl-[7-(toluene-3-sulfonyl)-2,3-dihydro-benzo[1,4]dioxin-2-ylmethyl]-amine;
Methyl-[7-(toluene-2-sulfonyl)-2,3-dihydro-benzo[1,4]dioxin-2-ylmethyl]-amine;
1-(7-Benzenesulfonyl-2,3-dihydro-benzo[1,4]dioxin-2-ylmethyl)-piperazine;
N-(7-Benzenesulfonyl-2,3-dihydro-benzo[1,4]dioxin-2-ylmethyl)-guanidine;
N-(7-Benzenesulfonyl-2,3-dihydro-benzo[1,4]dioxin-2-ylmethyl)-N-methyl-hydroxylamine;
1-(7-Benzenesulfonyl-2,3-dihydro-benzo[1,4]dioxin-2-ylmethyl)-1H-imidazole;
N-(7-Benzenesulfonyl-2,3-dihydro-benzo[1,4]dioxin-2-ylmethyl)-acetamide;
2-(3-Methylaminomethyl-2,3-dihydro-benzo[1,4]dioxine-6-sulfonyl)-benzonitrile;
1-(7-Benzenesulfonyl-2,3-dihydro-benzo[1,4]dioxin-2-ylmethyl)-pyrrolidin-3-ol;
3-(3-Methylaminomethyl-2,3-dihydro-benzo[1,4]dioxine-6-sulfonyl)-benzonitrile;
(7-Benzenesulfonyl-2-methyl-2,3-dihydro-benzo[1,4]dioxin-2-ylmethyl)-methyl-amine;
(7-Benzenesulfonyl-2,3-dihydro-benzo[1,4]dioxin-2-ylmethyl)-urea;
[2-(6-Benzenesulfonyl-2,3-dihydro-benzo[1,4]dioxin-2-yl)-ethyl]-methyl-amine; and
[2-(7-Benzenesulfonyl-2,3-dihydro-benzo[1,4]dioxin-2-yl)-ethyl]-methyl-amine.

23. A pharmaceutical composition comprising an effective amount of the compound of claim 1 in admixture with a pharmaceutically acceptable carrier.

\* \* \* \* \*